United States Patent
Cunningham et al.

(10) Patent No.: US 11,654,429 B2
(45) Date of Patent: May 23, 2023

(54) SYSTEM FOR RAPID, PORTABLE, AND MULTIPLEXED DETECTION AND IDENTIFICATION OF PATHOGEN SPECIFIC NUCLEIC ACID SEQUENCES

(71) Applicant: THE BOARD OF TRUSTEES OF THE UNIVERSITY OF ILLINOIS, Urbana, IL (US)

(72) Inventors: Brian T. Cunningham, Champaign, IL (US); Rashid Bashir, Champaign, IL (US); Anurup Ganguli, Urbana, IL (US); Akid Ornob, Champaign, IL (US); Gregory Damhorst, Elgin, IL (US); Hojeong Yu, Savoy, IL (US); Weili Chen, Sunnyvale, CA (US); Fu Sun, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 608 days.

(21) Appl. No.: 16/495,614

(22) PCT Filed: Mar. 20, 2018

(86) PCT No.: PCT/US2018/023338
§ 371 (c)(1),
(2) Date: Sep. 19, 2019

(87) PCT Pub. No.: WO2018/175424
PCT Pub. Date: Sep. 27, 2018

(65) Prior Publication Data
US 2020/0023360 A1    Jan. 23, 2020

Related U.S. Application Data

(60) Provisional application No. 62/616,151, filed on Jan. 11, 2018, provisional application No. 62/474,787, filed on Mar. 22, 2017.

(51) Int. Cl.
*B01L 7/00* (2006.01)
*C12Q 1/6844* (2018.01)
(Continued)

(52) U.S. Cl.
CPC .......... *B01L 3/502715* (2013.01); *B01L 7/52* (2013.01); *C12Q 1/6844* (2013.01); *G01N 21/01* (2013.01);
(Continued)

(58) Field of Classification Search
CPC .......... G01N 2021/6471; G01N 21/01; G01N 2201/0221; G01N 21/6428;
(Continued)

(56) References Cited

U.S. PATENT DOCUMENTS

2012/0168305 A1   7/2012  Hunter
2013/0157351 A1*  6/2013  Ozcan .................. H04N 5/2254
                                                     422/69
(Continued)

FOREIGN PATENT DOCUMENTS

JP    2006238094 A  *  9/2006
WO    2009/047804 A2    4/2009
(Continued)

OTHER PUBLICATIONS

Damhorst et al., "Smartphone-Imaged HIV-1 Reverse-Transcription Loop-Mediated Isothermal Amplification (RT-LAMP) on a Chip from Whole Blood", Engineering, vol. 1, No. 3, pp. 324-335. (Year: 2015).*
(Continued)

*Primary Examiner* — Young J Kim
(74) *Attorney, Agent, or Firm* — McDonnell Boehnen Hulbert & Berghoff LLP

(57) ABSTRACT

A sample carrier may include a sample preparation module and an amplification module. A sample mixes with a lysis
(Continued)

medium and a nucleic acid amplification medium in the sample preparation module and then flows into a plurality of microfluidic chambers in the amplification module. The microfluidic chambers have disposed therein primers configured to initiate amplification of one or more target nucleic acid sequences corresponding to one or more pathogens. The sample carrier is inserted into an apparatus that includes a plurality of Sight sources and a camera. The light sources illuminate the microfluidic chambers with excitation light, a fluorophore emits fluorescence light indicative of nucleic acid amplification in response to the excitation-light, and the camera captures images of the microfluidic chambers. A target nucleic acid sequence in the sample is indicated by the images showing an increasing fluorescence in a microfluidic chamber that has the primers for that sequence.

20 Claims, 25 Drawing Sheets

(51) Int. Cl.
   *B01L 3/00* (2006.01)
   *G01N 21/01* (2006.01)
   *G01N 21/64* (2006.01)

(52) U.S. Cl.
   CPC ..... *G01N 21/6428* (2013.01); *G01N 21/6452* (2013.01); *G01N 21/6456* (2013.01); *B01L 2200/10* (2013.01); *B01L 2200/16* (2013.01); *B01L 2300/06* (2013.01); *B01L 2300/0809* (2013.01); *B01L 2300/1805* (2013.01); *B01L 2400/0487* (2013.01); *B01L 2400/06* (2013.01); *G01N 2021/6439* (2013.01); *G01N 2021/6471* (2013.01)

(58) Field of Classification Search
   CPC ....... G01N 21/6456; G01N 2021/6439; G01N 21/6452; G01N 21/64; C12Q 1/6844; C12Q 2563/107; C12Q 2565/629; B01L 2200/10; B01L 3/5027
   See application file for complete search history.

(56) References Cited

U.S. PATENT DOCUMENTS

2013/0260372 A1    10/2013  Buermann et al.
2017/0001196 A1*   1/2017   Zhang ............... B01L 3/502738

FOREIGN PATENT DOCUMENTS

WO    WO-2014127379 A1 *  8/2014  ............. B01L 3/021
WO    2015/061480 A1      4/2015
WO    2015/073384 A1      5/2015

OTHER PUBLICATIONS

Michael Seidel et al., "Automated analytical microarrays: a critical review," Anal Bioanal. Chem., vol. 391, No. 5, pp. 1521-1544 (2008).
The International Search Report (ISR) with Written Opinion for PCT/US2018/023338 dated Aug. 8, 2018, pp. 1-19.
Damhorst, Gregory L. et al. "Smartphone-Imaged HIV-1 Reverse-Transcription Loop-Mediated Isothermal Amplification (RT-LAMP) on a Chip from Whole Blood" Engineering (2015) vol. 1(3), pp. 324-335.

* cited by examiner

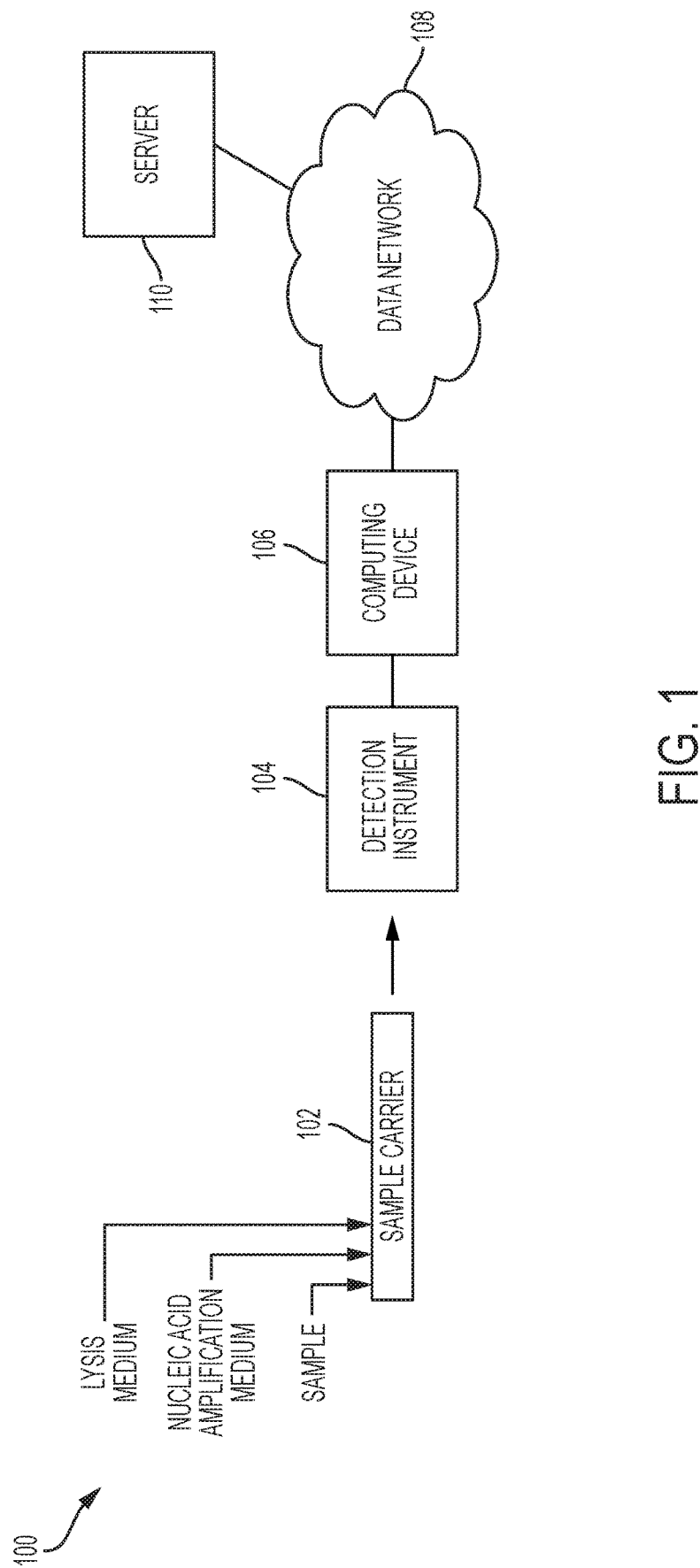

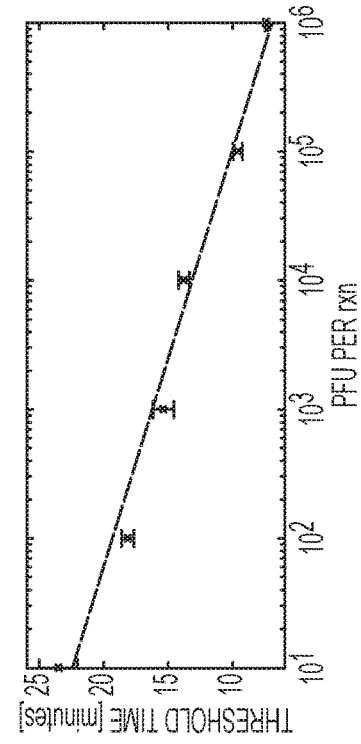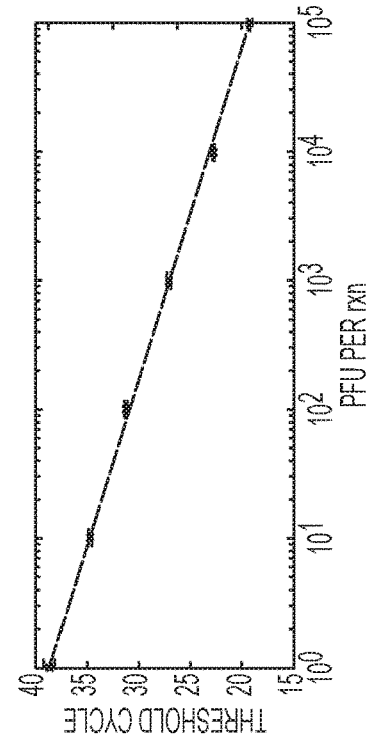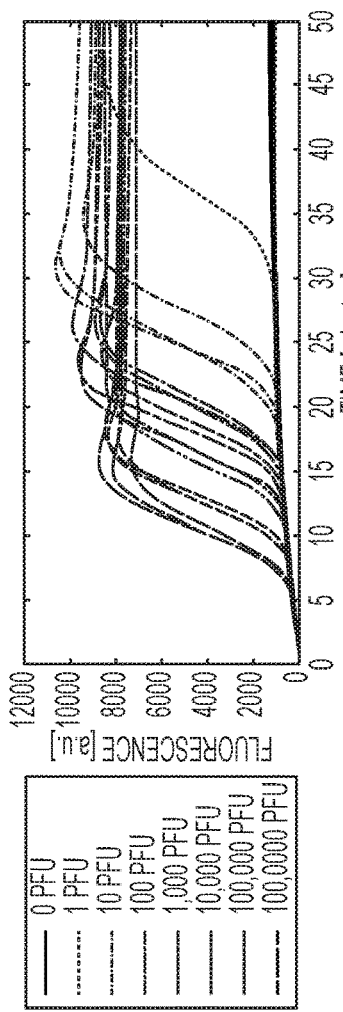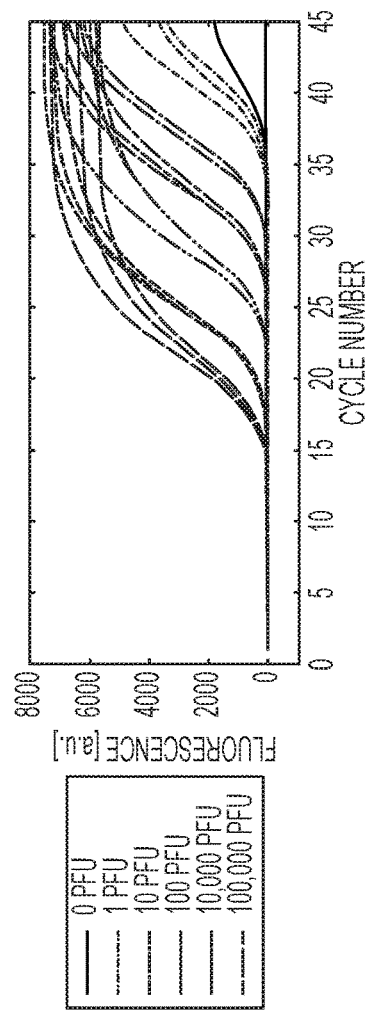
FIG. 12A
FIG. 12B
FIG. 12C
FIG. 12D

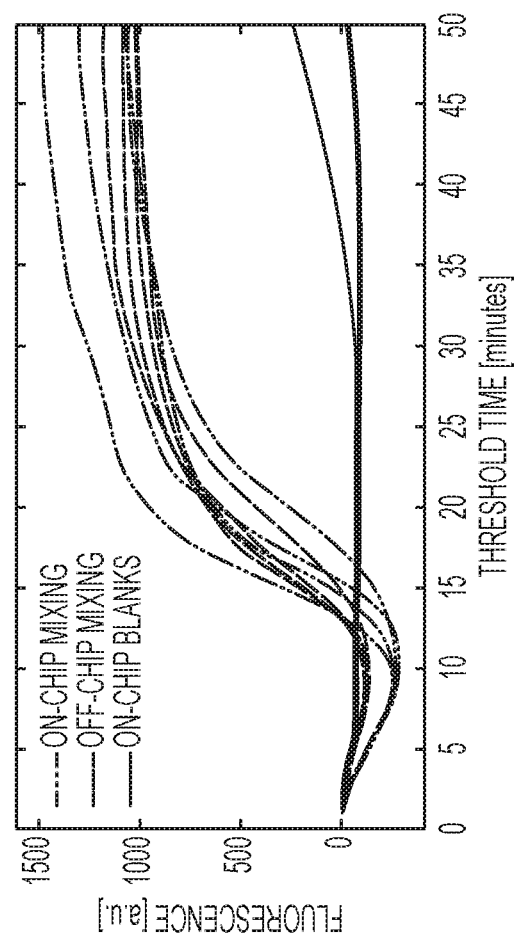
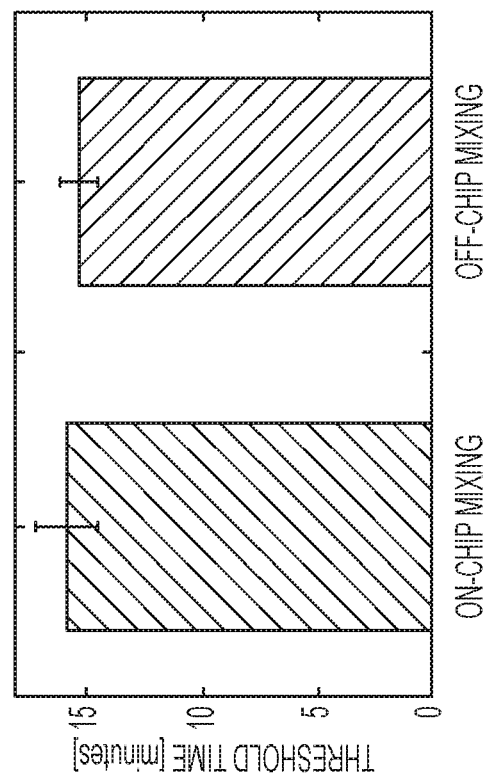
FIG. 14A
FIG. 14B

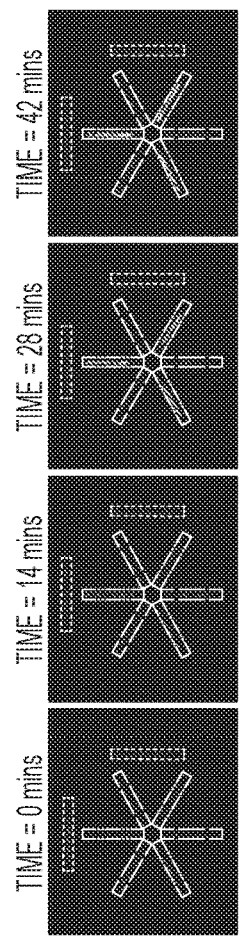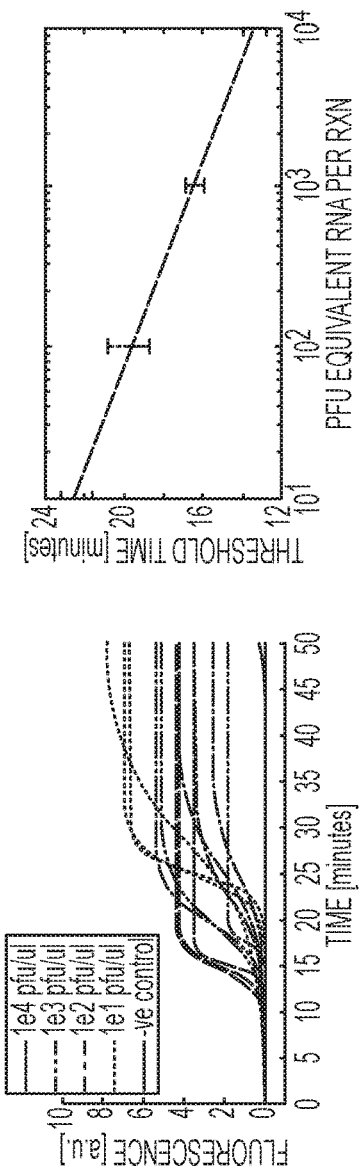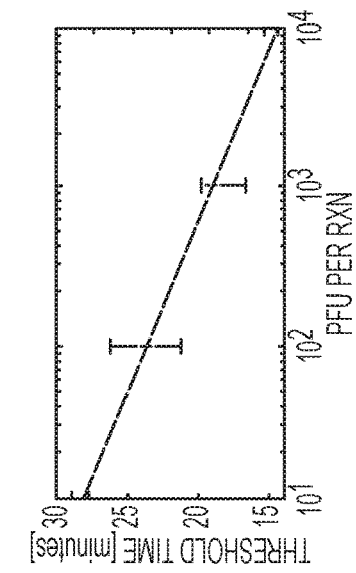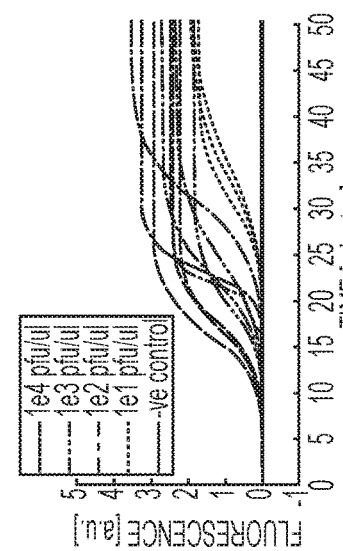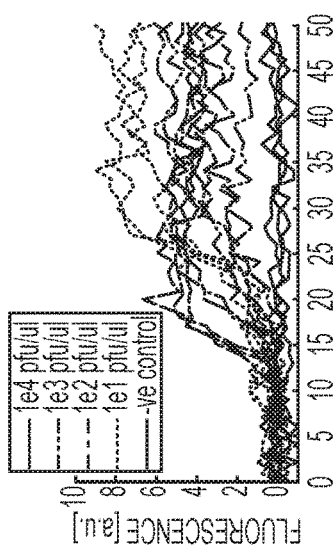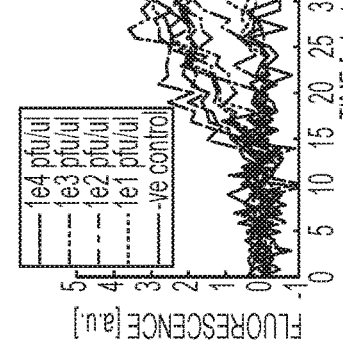

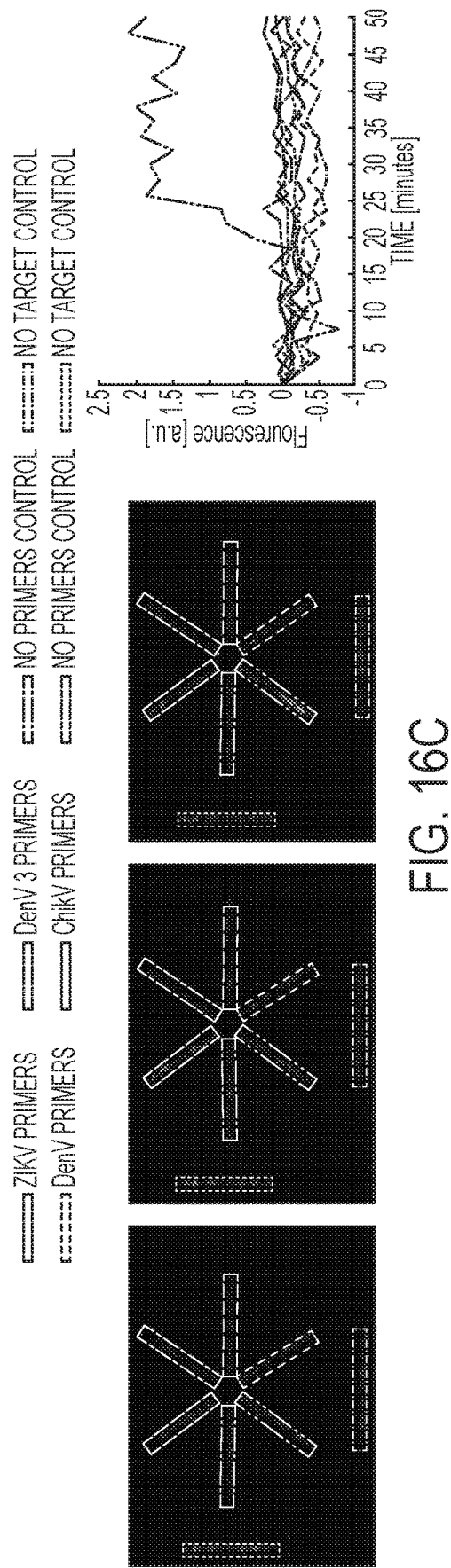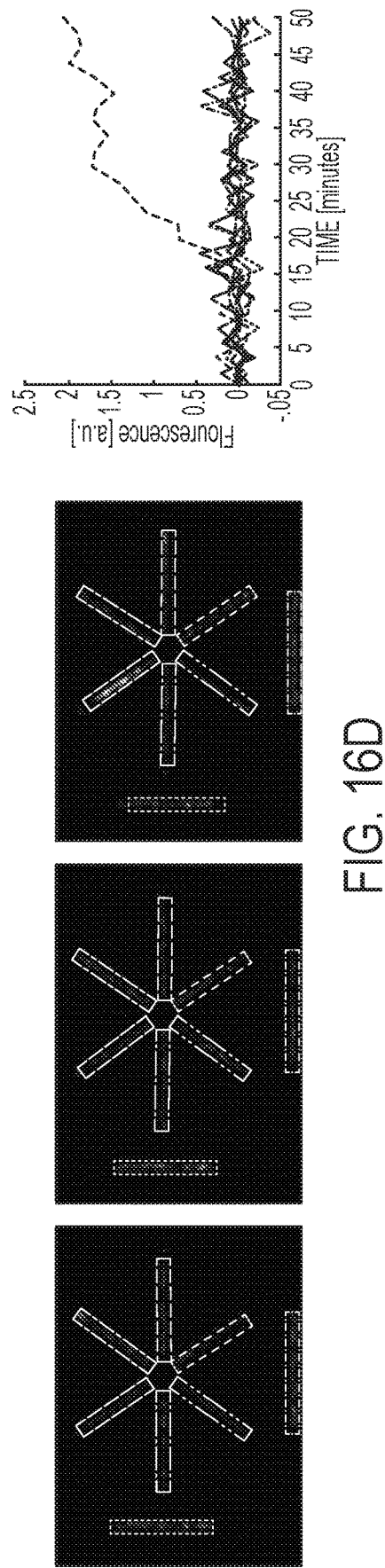
FIG. 16C
FIG. 16D

SYSTEM FOR RAPID, PORTABLE, AND MULTIPLEXED DETECTION AND IDENTIFICATION OF PATHOGEN SPECIFIC NUCLEIC ACID SEQUENCES

CROSS-REFERENCE TO RELATED APPLICATIONS

This application is a national stage application under 35 U.S.C. § 371 of International Application No. PCT/US2018/023338, filed Mar. 20, 2018, which claims priority to U.S. Provisional Application No. 62/616,151, filed Jan. 11, 2018 and U.S. Provisional Application No. 62/474,787, filed Mar. 22, 2017, all of which are hereby incorporated by reference in their entirety.

STATEMENT REGARDING FEDERALLY SPONSORED RESEARCH

This invention was made with government support under CBET 1264377 awarded by the National Science Foundation. The government has certain rights in the invention.

BACKGROUND

Infectious diseases, such as HIV/AIDS, tuberculosis, and malaria, while accounting for less than 10% of deaths in the developed world, are responsible for more than half of all deaths in developing countries. A contributing factor to the mortality of infectious diseases in developing countries is that co-infection by more than one pathogen carries greater risk than a single infection, while many assays that only test for one agent will miss the presence of a co-infection. Despite recent progress in the development of new drugs for treatment of viral, bacterial, and fungal infections, the worldwide death toll continues to rise with critical needs for increased understanding of fundamental disease mechanisms, and enhanced point-of-care diagnostics. Importantly, there is a need for improved surveillance tools that can detect the emergence of drug resistance, alert clinicians to the initiation of a potential outbreak, monitor the effectiveness of quarantines, and facilitate cross-communication between clinicians that are geographically distributed. For human infectious diseases in the United States, approximately 55 are designated as "reportable" by the Center for Disease Control, which requires a positive laboratory test to be communicated to central authorities, although the information is reported to clinicians by the National Notifiable Diseases Surveillance System (NNDSS), which is most heavily utilized only for the most deadly disease outbreaks. Most forms of influenza have no reporting requirement, and thus no information is gathered or communicated for human respiratory infectious diseases that are responsible for 2-3 million cases and 250,000-500,000 deaths worldwide each year. Reporting requirements are even more rudimentary in the developing world, leaving clinicians largely unaware of the global view of incidence, spread, and control of infectious disease that affects their community.

The societal and economic toll of infectious disease is not limited only to human populations. Animals raised for human consumption live in facilities in which large herds share ventilation, feed, and waste handling within confined spaces in which respiratory infectious disease can spread rapidly. Similar concerns exist for companion animals and racing animals, particularly for those with high economic value. In veterinary medicine in the United States, only a handful of infectious diseases are categorized as "reportable" by the USDA, requirements vary from state to state, and no cross-communication infrastructure exists that enables veterinarians to easily share results with each other.

A key characteristic for a successful system for detection and reporting of infectious disease is speed. For example, modeling studies on various intervention strategies for pandemic influenza response have shown that the highest impact on attack rate is obtained by identification and initiation of treatment one day earlier. Particularly for point-of-care scenarios, where the clinician is testing a patient at a remote clinic, a farm, or a racetrack, the involved to send samples to a central laboratory, wait for the test to be performed, and wait is for the results to be reported, results in an enormous waste of opportunity to determine if aggressive treatment or quarantine is needed before the disease spreads further. The ability to rapidly share the results of positive and negative tests will revolutionize the manner in which infectious diseases are managed. Therefore, it is highly advantageous for the test to be performed at the same location as the patient, so action can be taken within the same day as the sample is gathered.

Taking advantage of the fact that bacteria and viruses have distinct genetic components that are represented by unique nucleic acid sequences, the most commonly used laboratory analysis technique used for diagnosis of infectious disease is the Polymerase Chain Reaction (PCR). PCR enables sequence-specific concentration amplification of infectious disease DNA through a series of thermally cycled chemical reactions between a set of enzymes, a prepared test sample (of DNA extracted from a pathogen-containing bodily fluid), and disease-specific "primer" molecules. PCR primers for detection of common human and animal infectious disease have been identified, and may be inexpensively synthesized through readily available commercial sources. Conventional PCR amplification typically involves expensive laboratory-based instruments that are operated by technicians and housed in central facilities, although there have been strong efforts aimed at miniaturization of PCR for translation closer to the point of care through the engineering of systems integrated into a small chip or cartridge. Many of these efforts have been aimed at accelerating the thermal cycling process through reduction in the liquid volume, while others have explored various modalities for sensing the presence of the amplified product using biosensors. Due to the cost and complexity of implementing thermal cycling—which generally involves cycling between 95° C. (denaturation), 72° C. (extension), and 68° C. (annealing) with about 30-40 cycles—various isothermal nucleic acid amplification methods have been proposed and demonstrated with comparable sensitivity to PCR. Of these, loop-mediated Isothermal amplification (LAMP) has emerged as the favored approach for portable applications. Details of the LAMP process, primer design, and example applications are thoroughly explained in the published literature. See, e.g., M. Parida, S. Sannarangaiah, P. K. Dash, P. V. L. Rao, and K. Morita, "Loop mediated isothermal amplification (LAMP): a new generation of innovative gene amplification technique, perspectives in clinical diagnosis of infectious diseases," *Reviews in Medical Virology* vol. 18, pp. 407-421, November-December 2008.

An important consideration for the widespread adoption of Point-of-Care (POC) tests is the availability of detection instruments that are inexpensive, portable, and able to share data wirelessly over the internet. Due to the rapid development of computational, communication, and sensing capabilities of smartphones since the introduction of the iPhone in 2007, these devices have become similar to personal computers with integrated cameras, geolocation capabilities, and access to the internet. Since 2011, over 478 million smartphones are sold annually, with that number expected to double in the next 4 years, making them a nearly ubiquitous tool that can be adapted to performing POC tests. Recent examples include attachments that enable smartphones to serve as stethoscopes, ultrasound probes, microscopes, fluorescent microscopes, label-free biosensor detection instruments, fluorimeters, and ELISA assay readers. Portable detection systems for infectious disease are already recognized as a likely extension of mobile technology, although to date there is no existing PCR or LAMP mobile sensing platform that is integrated with a smartphone and a smart service system for reporting and sharing results with a network of users.

SUMMARY

In a first aspect, example embodiments provide an apparatus for optically interrogating a sample in a sample carrier, the sample carrier comprising a plurality of microfluidic chambers, each of the microfluidic chambers containing a respective portion of the sample mixed with a nucleic acid amplification medium. The apparatus comprises a housing, a plurality of light sources coupled to the housing, and a camera coupled to the housing. The housing has an interior space and a slot through which the interior space is accessible, wherein the slot is configured to receive the sample carrier such that the microfluidic chambers are disposed at a working position within the interior space. Each of the light sources is configured to illuminate the microfluidic chambers disposed at the working position with excitation light, and a fluorophore in the nucleic acid amplification medium is configured to emit fluorescence light indicative of nucleic acid amplification in response to the excitation light. The camera is configured to capture images of the microfluidic chambers disposed at the working position.

In a second aspect, example embodiments provide a sample carrier comprising a card and an amplification module mounted on the card. The amplification module comprises an amplification-module inlet for receiving a sample and a nucleic acid amplification medium and a plurality of microfluidic chambers fluidly coupled to the amplification-module inlet, wherein one or more of the microfluidic chambers have disposed therein primers configured to initiate amplification of one or more target nucleic acid sequences, wherein the nucleic acid amplification medium comprises a fluorophore configured to emit fluorescence light indicative of nucleic acid amplification in response to excitation light, wherein the amplification module has a first surface coupled to the card and a second surface opposite the first surface, and wherein the first surface is transparent to the excitation light and the fluorescence light.

In a third aspect, example embodiments provide a method. The method involves providing a sample carrier comprising an amplification module mounted on a card, wherein the amplification module comprises an amplification-module inlet and a plurality of microfluidic chambers fluidly coupled to the amplification-module inlet, wherein one or more of the microfluidic chambers have disposed therein primers configured to initiate amplification of one or more target nucleic acid sequences. The method further involves applying a sample and a nucleic acid amplification medium to the amplification-module inlet, wherein a respective portion of the sample and the nucleic acid amplification medium flows from the amplification-module inlet into each of the microfluidic chambers. The method additionally involves inserting the sample carrier with the sample and nucleic acid amplification medium contained therein into an apparatus, wherein the apparatus comprises a plurality of light sources and a camera. The method also involves capturing, using the camera, at least one image of the microfluidic chambers while the microfluidic chambers are being illuminated with excitation light emitted by the light sources, wherein a fluorophore in the nucleic acid amplification medium is configured to emit fluorescence light indicative of nucleic acid amplification in response to the excitation light. And the method involves determining whether any of the one or more target nucleic acid sequences are present in the sample based on the at least one image.

BRIEF DESCRIPTION OF THE DRAWINGS

FIG. 1 is a schematic illustration of a system that includes a sample carrier, a detection instrument, a computing device, a data network, and a server, in accordance with an example embodiment.

FIGS. 12A-12F show the results of experiments performed in a benchtop thermocycler apparatus, the results including: curves that represent the baseline-subtracted change in fluorescent intensity over time in a RT-LAMP assay for different concentrations of Zika RNA (FIG. 12A); a plot of the corresponding threshold time against the PFU equivalent of purified RNA per reaction (FIG. 12B); curves that represent the baseline-subtracted change in fluorescent intensity over time in a RT-PCR assay for different concentrations of Zika RNA (FIG. 12C); the corresponding standard curve for the RT-PCR assay (FIG. 12D); curves that represent the baseline-subtracted change in fluorescent intensity over time in a RT-LAMP assay for different concentrations of whole Zika viruses in lysed whole blood (FIG. 12E); and a plot of the corresponding threshold times for the different concentrations (FIG. 12F), in accordance with an example embodiment.

FIGS. 14A and 14B show the results of mixing whole blood spiked with Zika virus with lysis buffer and RT-LAMP reagents for on-chip mixing in a sample preparation module as shown in FIG. 3B and for off-chip mixing performed manually using a pipette, the results including: baseline-subtracted raw amplification curves showing the changes in fluorescence over time for outputs from the sample preparation module (on-chip mixing) and for the four replicates mixed manually (off-chip mixing) (FIG. 14A); and bar graphs comparing the threshold times determined from the curves (FIG. 14B), in accordance with an example embodiment.

FIGS. 15A-15G show the results of RT-LAMP assays performed in an amplification module as shown in FIG. 3C using a detection instrument as shown in FIGS. 5A, 5B, and 6, the results including: raw fluorescence images of the amplification module at time=0, 14, 28, and 42 minutes for samples containing purified Zika RNA (FIG. 15A); the raw amplification curves for the on-chip amplification of the Zika RNA (FIG. 15B); the amplification curves after sigmoidal fitting (FIG. 15C); the threshold-time standard curves for these reactions (FIG. 15D); the raw amplification curves carried out on-chip with whole Zika viruses in blood (FIG. 15E); the amplification curves after sigmoidal fitting (FIG. 15F); and the threshold-time standard curves for these reactions (FIG. 15G), in accordance with an example embodiment.

FIGS. 16A-16D show the results of RT-LAMP assays performed in an amplification module as shown in FIG. 3C using a detection instrument as shown in FIGS. 5A, 5B, and 6, including raw fluorescence images of the amplification module, together with raw amplification curves of the RT-LAMP reaction for samples of whole blood containing whole Zika virus (FIG. 16A), DENV-1 viral RNA (FIG. 16B), DENV-3 viral RNA (FIG. 16C), and CHIKV viral RNA (FIG. 16D), in accordance with an example embodiment.

DETAILED DESCRIPTION

1. Overview

Figure 2A:
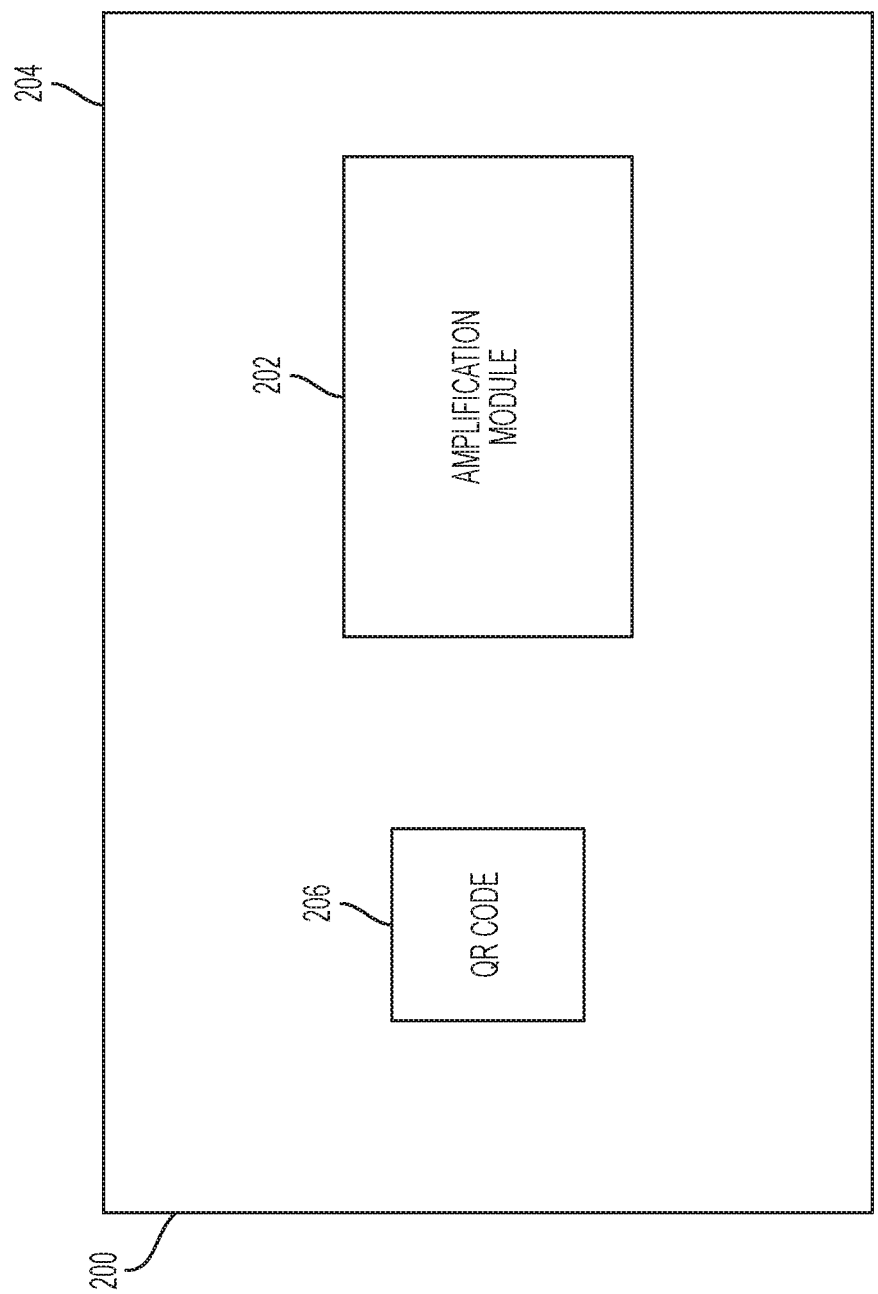
FIG. 2A is a schematic illustration of a sample carrier that includes an amplification module and a QR code on a card, in accordance with an example embodiment.

The present disclosure provides a system for automated detection, identification, analysis, and reporting of one or more target nucleic acid (DNA or RNA) sequences in a sample (e.g., a single drop of blood). The nucleic acid sequences may be selected to indicate the presence of viral, bacterial, or fungal pathogens. In example implementations, the system includes: (1) a sample carrier (e.g., with a form factor similar to a credit card) that includes a sample preparation module (in which cell lysis occurs to prepare the sample for nucleic acid amplification) and an amplification module with a plurality of microfluidic chambers that receive respective portions of the sample and in which amplification of nucleic acids in the sample can occur and be fluorescently monitored; (2) a detection instrument that optically interrogates the microfluidic chambers in the sample carrier to obtain one or more images of fluorescence light indicative of nucleic acid amplification; (3) software that operates to analyze the fluorescence images, determine fluorescence intensity within regions of interest, determine which nucleic acid sequences were present in the test sample, (optionally) estimate the concentration of each nucleic acid sequence that was determined to be present, and upload the results of tests to a cloud-based service system; and (4) a cloud-based service system that enables a user to observed the outcomes of tests performed by other users (e.g., using their own sample carriers and detection instruments). The other users can be selected and displayed using selected criteria, such as type of pathogen, geographic location of the test, patient-specific information (e.g., gender, age, breed of animal), and timeframe (e.g., week, month, year). The service system may be configured to deliver messages when specific types of positive tests have been registered by other users.

The disclosure provides for portable diagnostic testing for viral, bacterial, or fungal pathogens. The system is intended to be used in situations in which an immediately available test result is desired (for example, for identification of the presence of highly infectious diseases) where the alternative would be to gather a sample, and send it to a remote laboratory facility for testing. The purpose of the rapid, point of care test is to avoid the consequences of a contagious individual to infect additional people or animals. An additional purpose is to provide a testing capability in locations where a laboratory facility is not available, but in which test results can be shared with a remotely located physician or regulatory authority. A further purpose is to perform tests for multiple pathogens within a single test sample, in which a set of tests that represent a panel of common causes of illness or likely sets of pathogens are of interest. Yet a further purpose is to enable such tests to be performed with minimal intervention from the user, such that the chemical reactions, sensing, and image analysis are automated.

The sample carrier and detection instrument herein can be inexpensive and highly portable (e.g., handheld). The detection instrument can use the camera in a conventional smartphone or include an image sensor that communicates images to a smartphone via wireless data transmission or a hardwired connection to a smariphone's data port. The sample carriers can be configured to assay several different types of nucleic acid sequences, for example, representing panels of tests that are grouped together for specific types of customers. The samples carriers can also be configured to incorporate positive and negative controls, for example, to serve as references against user error, reagent failure, and variability from one measurement to the next. The sample carriers can be customized for detection of new nucleic acid sequences, for example, nucleic acid sequences representing a newly emerging virus. In some examples, the sample carrier may be used to detect nucleic acid sequences in a very small sample, such as a blood sample that is less than 50 microliters, less than 20 microliters, or less than 10 microliters. In some examples, the sample carrier may have a form factor similar to a conventional credit card and may include information about the test stored in a magnetic strip, bar code, QR code, RFID tag, or other type of data storage in the sample carrier that can be read by the detection instrument or other device. The detection of nucleic acid sequences can be either qualitative (e.g., resulting in a positive or negative result for each nucleic acid sequence assayed) or quantitative (resulting in a concentration for each nucleic acid sequence assayed). The nucleic acid amplification can be fluorescently monitored by obtaining multiple images over time, for example, to determine an endpoint of the reaction and/or to allow curve-fitting of the resulting increase in fluorescence over time. The test protocols can be highly automated, with the user adding the test sample and reagents to the sample carrier and the software controlling the camera to obtain and process the images to determine the results.

Applications of the present disclosure include, but are not limited to, human infectious disease diagnosis (HIV, Zika, Dengue, Chikungunya), animal infectious disease diagnosis (equine, bovine, swine, canine, avian, etc.), bacterial or viral contamination of water resources, food safety in restaurants, food processing, food storage, and food transport, pharmaceutical quality control, mobile veterinary laboratory, and biowarfare agent defense.

2. Example System

FIG. 1 schematically illustrates an example system 100 that includes a sample carrier 102, a detection instrument 104, a computing device 106, a data network 108, and a server 110. The sample carrier 102 is configured to receive a sample and to amplify one or more different types of nucleic acid sequences that may be present in the sample. To measure the amplified nucleic acids, the sample carrier 102 is inserted into detection instrument 104. The detection instrument 104 is configured to optically interrogate the sample carrier 102 to detect the amplified nucleic acid sequences in the sample carrier 102 (e.g., based on fluorescent light indicative of amplified nucleic acids).

The amplification may occur in a plurality of microfluidic chambers in an amplification module in the sample carrier 102. Each of the microfluidic chambers may have disposed therein primers for initiating amplification of a target nucleic acid sequence, for example, a nucleic acid sequence that represents a specific viral, bacterial, or fungal pathogen. Different primers may be loaded in different microfluidic chambers, so that sample carrier 102 may be configured to amplify a plurality of different target nucleic acid sequences in parallel (e.g., a multiplexed array of 1-10 pathogen-specific nucleic acid sequences). In some examples, primers for amplifying a nucleic acid sequence may be disposed in more than one of the microfluidic chambers, so that duplicate tests for a target nucleic acid sequence can be performed using sample carrier 102. In addition, one or more of the microfluidic chambers can serve as a positive control (e.g., loaded with a nucleic acid sequence and primers configured to amplify that sequence) and one or more of the microfluidic chambers can serve as a negative control (e.g., by not including any primers).

The amplification of nucleic acids in sample carrier 102 may involve the polymerase chain reaction (PCR), loop-mediated isothermal amplification (LAMP), or some other technique. The reagents for the nucleic acid amplification (described herein as a "nucleic acid amplification medium") may be applied to the sample carrier 102 along with the sample. For example, the nucleic acid amplification medium could be applied to the sample carrier 102 before the sample is applied, after the sample is applied, or the sample and nucleic acid medium could be applied together as a mixture. Alternatively, the sample carrier 102 may be pre-loaded with a predetermined amount of nucleic acid amplification medium.

The detection instrument 104 can provide temperature control for the nucleic acid amplification. For example, after applying the sample and nucleic acid amplification medium to the sample carrier 102, the sample carrier 102 may be inserted into the detection instrument 104 so that the microfluidic chambers are in thermal contact with a heating device in the detection instrument 104. The heating device may maintain a predetermined temperature within the microfluidic chambers for LAMP or may perform temperature cycling for PCR. Alternatively, a heating device for the temperature control may be separate from the detection instrument 104.

The nucleic acid medium may include a fluorophore that can be used to monitor the nucleic acid amplification process. For example, the fluorophore could be an intercalating dye (e.g., SYBR Green dye or EvaGreen dye) that is essentially non-fluorescent when unbound and becomes brightly fluorescent when incorporated into amplified nucleic acids, i.e., double-stranded DNA (dsDNA) or double-stranded RNA (dsRNA). Thus, the fluorescence light emitted by the intercalating dye (in response to excitation light) is indicative of nucleic acid amplification, with the fluorescence intensity increasing as the amount of amplified nucleic acid increases.

The sample that is applied to the sample carrier 102 could be a sample of blood, urine, stool, or other bodily fluid or material. In some implementations, the sample carrier 102 is configured to receive a sample that has already been processed to release nucleic acids (e.g., by lysing) contained in infected host cells, bacterial cells, viral particles, or other pathogens present in the sample. In other implementations, the sample carrier 102 is configured to receive an unprocessed sample (e.g., a droplet of whole blood). In such implementations, the sample carrier 102 may include a sample preparation module that is fluidly coupled to the amplification module. The unprocessed sample is applied to the sample preparation module along with a lysis medium that is configured to perform cell lysing as the unprocessed sample and lysis medium mix together and flow through the sample preparation module. In this way, the sample preparation module may produce a processed sample suitable for nucleic acid amplification that then flows into the amplification module. The lysis medium could be applied to the sample carrier 102 before the unprocessed sample is applied, after the unprocessed sample is applied, or the unprocessed sample and lysis medium could be applied together as a mixture. Alternatively, the sample carrier 102 may be pre-loaded with a predetermined amount of lysis medium.

As noted above, the detection instrument 104 is configured to optically interrogate the sample carrier 102 to detect amplified nucleic acids in the microfluidic chambers. In example embodiments, the detection instrument 104 detects amplified nucleic acids by detecting fluorescence light that is indicative of nucleic acid amplification, thereby making use of the property that certain fluorophores, such as intercalating dyes, emit fluorescence light in response to excitation light when incorporated into amplified nucleic acids. In such embodiments, the detection instrument 104 may include one or more light sources that emit the excitation light and a camera that can capture images that include the fluorescence light emitted by the fluorophore in response to the excitation light. For example, the detection instrument 104 may include a slot through which the sample carrier 102 can be inserted such that the microfluidic chambers are placed at a working position within the detection instrument 104. At this working position, the one or more light sources emit the excitation light toward the microfluidic chambers and the microfluidic chambers are also in the field of view of the camera. In this way, the camera can capture images of the microfluidic chambers that include fluorescence light by the fluorophore emitted in response to the excitation light.

The computing device 106 may be programmed to control the camera in the detection instrument 104 to capture the images and to analyze the captured images to determine whether one or more target nucleic acid sequences are present in the sample contained in the sample carrier 102. In some implementations, the computing device 106 is a mobile computing device, such as a smartphone, that is mounted to the detection instrument 104. In such implementations, the camera that is used to capture images may be part of the computing device 106. In other implementations, the camera is part of the detection instrument 104 and conununicates with the computing device 106 via a wired or wireless connection.

Computing device 106 can communicate with a cloud-based service, exemplified in FIG. 1 by server 110, via the data network 108. The data network 108 could be the Internet or any other type of data communication network. The server 110 can provide for data storage, management, and analysis of test results from multiple detection instruments at multiple locations. Further, authorized users may be able to query the server 110 about tests that have been performed and/or to receive alerts regarding tests that have been performed (e.g., tests that indicate emergence of a particular pathogen in a particular geographic area). The server 110 could support other cloud-based services as well.

3. Example Sample Carriers

FIG. 2A illustrates an example sample carrier 200. In this example, sample carrier 200 includes an amplification module 202 mounted on a card 204. The card 204 has the size and shape of a conventional credit card (85.6 mm long, 54.0 mm wide, and 0.8 mm thick) and is preferably made from a plastic material that has low auto-fluorescence, such as polyoxymethylene (POM). The amplification module 202 can be attached to the card 204 by an adhesive or other means.

Figure 2B:
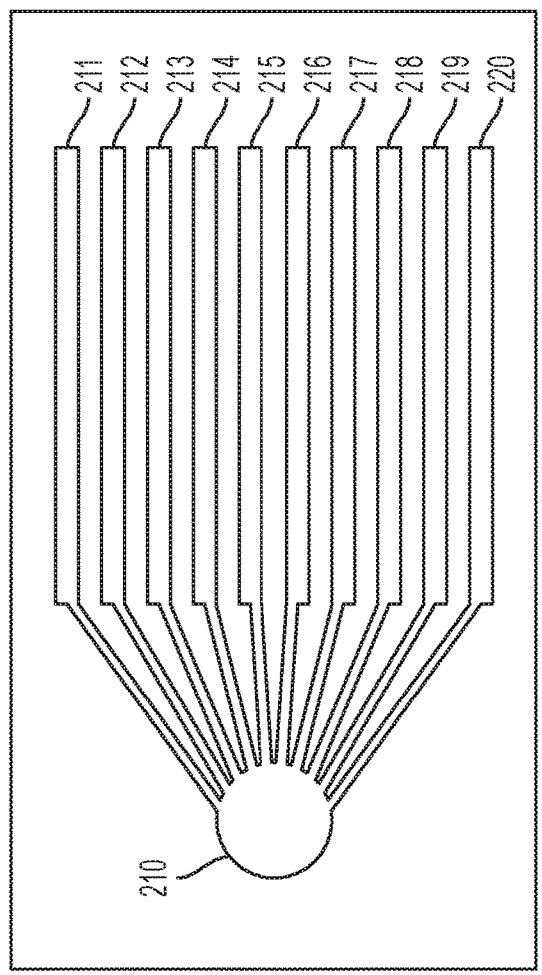
FIG. 2B is a top view of the amplification module shown in FIG. 2A, in accordance with an example embodiment.
Figure 2C:
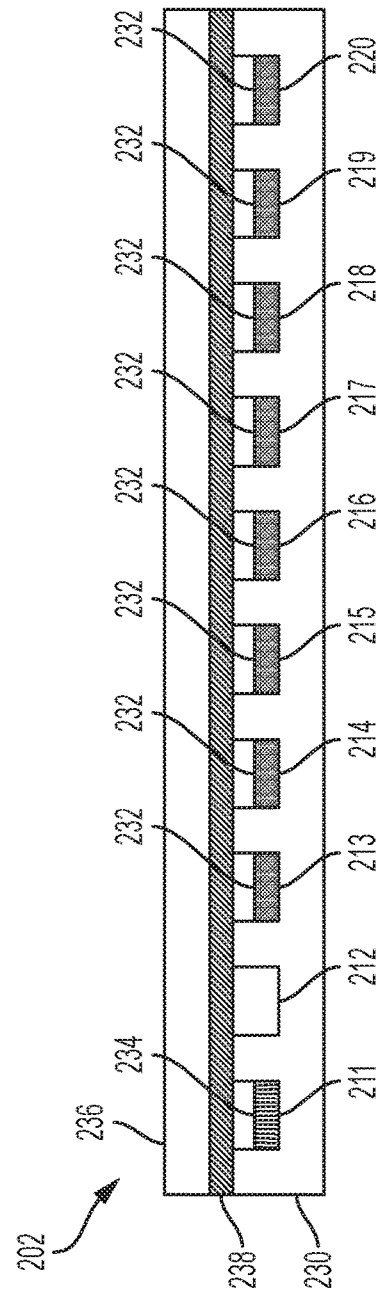
FIG. 2C is a cross-sectional view of the amplification module shown in FIGS. 2A and 2B, in accordance with an example embodiment.

FIGS. 2B and 2C illustrate an example configuration of amplification module 202. In this example, amplification module 202 includes a microfluidic structure that is formed in a silicon chip and sealed by a transparent cover. The silicon chip has the size and shape of a standard Subscriber Identify Module (SIM) card (25 mm long and 15 mm wide). FIG. 2B is a view of the microfluidic structure through the transparent cover. As shown in FIG. 2B, the microfluidic structure includes a sample inlet 210 that is fluidly connected to a plurality of microfluidic chambers in the form of ten flow channels 211-220 arranged in parallel. In this example, the sample inlet 210 has a diameter of 4 mm, and each of the flow channels 211-220 is 10 mm in length, 500 µm in width, and 200 µm in depth, representing a volume of 1 microliter each. With this configuration, the sample inlet 210 can accept a fluid sample of about 15 microliters that then flows into each of the flow channels 211-220 so as to be evenly distributed therein.

FIG. 2C is a cross-sectional view of the amplification module 202 through the flow channels 211-220. As shown in FIG. 2C, flow channels 211-220 are formed in a silicon substrate 230. Preferably, the silicon substrate 230 is oxidized to provide a thin film (e.g., 200 nm) of $SiO_2$ on the exposed surfaces. In this way, fluid in the flow channels 211-220 are in contact with $SiO_2$ rather than bare silicon, which can have an inhibitory effect on nucleic acid amplification. At least some of the flow channels 211-220 contain primers 232 that are configured to initiate amplification of one or more target nucleic acid sequences. In the example shown in FIG. 2C, primers 232 are disposed in each of flow channels 213-220. The primers 232 disposed in flow channels 213-220 could all be for amplifying the same target nucleic acid sequence, or the primers 232 disposed in different flow channels could be for amplifying different target nucleic acid sequences. In an illustrative example described below as Example Application 1, the primers 232 disposed in flow channels 213-220 can be used for the detection of four important vectors of equine infectious respiratory diseases: *Streptococcus equi* (S. Equi), *Streptococcus zooepidemicus* (S. Zoo), and Equine herpesvirus type 1 and type 4 (EHV-1 and EHV-4), with primers for S. Equi disposed in channels 213 and 214, primers for S. Zoo disposed in channels 215 and 216, primers for EHV-1 disposed in channels 217 and 218, and primers for EHV-4 disposed in channels 219 and 220.

The flow channels 211-220 can also include a flow channel that serves as a positive control and a flow channel that serves as a negative control. In the example shown in FIG. 3B, flow channel 211 contains a positive control mixture 234 so as to serve as a positive control, and flow channel 212 does not contain any primers so as to serve as a negative control. The positive control mixture 234 comprises a set of primers and the primers' corresponding target nucleic acid sequence (e.g., the primers and corresponding target nucleic acid sequence for S. Zoo). Fluorescence from the positive control can be used to confirm that the microfluidic channels have been filled with fluid and that the thermal conditions required for nucleic acid amplification have been achieved. Using a negative control with no primer enables determination of a background fluorescence level with no self-fluorescence from primers.

The primers 232 can be deposited into the flow channels 213-220 and the positive control mixture 234 can be deposited in flow channel 211 (e.g., by pipetting) and allowed to dry before a sample is applied to the sample inlet 210. After a sample is applied to the sample inlet 210, the flow channels 211-220 can be sealed by a transparent cover 236 (e.g., a glass coverslip) that is attached to the silicon substrate 230 by a transparent double-sided adhesive 238, as shown in FIG. 2C. Example Application 1 discussed below sets forth an example method of fabricating the amplification module 202 shown in FIGS. 2B and 2C. It is to be understood that the configuration of amplification module 202 shown in FIGS. 2B and 2C is exemplary only. For example, a greater or fewer number of flow channels could be provided. Further, the flow channels could be provided with different shapes and/or sizes than described above.

Turing again to FIG. 2A, the card 204 can also be provided with a Quick Response (QR) code 206 that encodes information about the sample carrier 200. Such information can include, for example, a serial number of the sample carrier, an identification of the target nucleic acid sequence or pathogen that can be detected in each flow channel, an identification of any flow channels that serve as positive or negative controls, the primer deposition date, and a use-by date. It is to be understood that other data could also be encoded in the QR code and that data could be stored on card 204 in other ways, for example, by using a magnetic strip, bar code, RFID tag or other means.

Figure 3A:
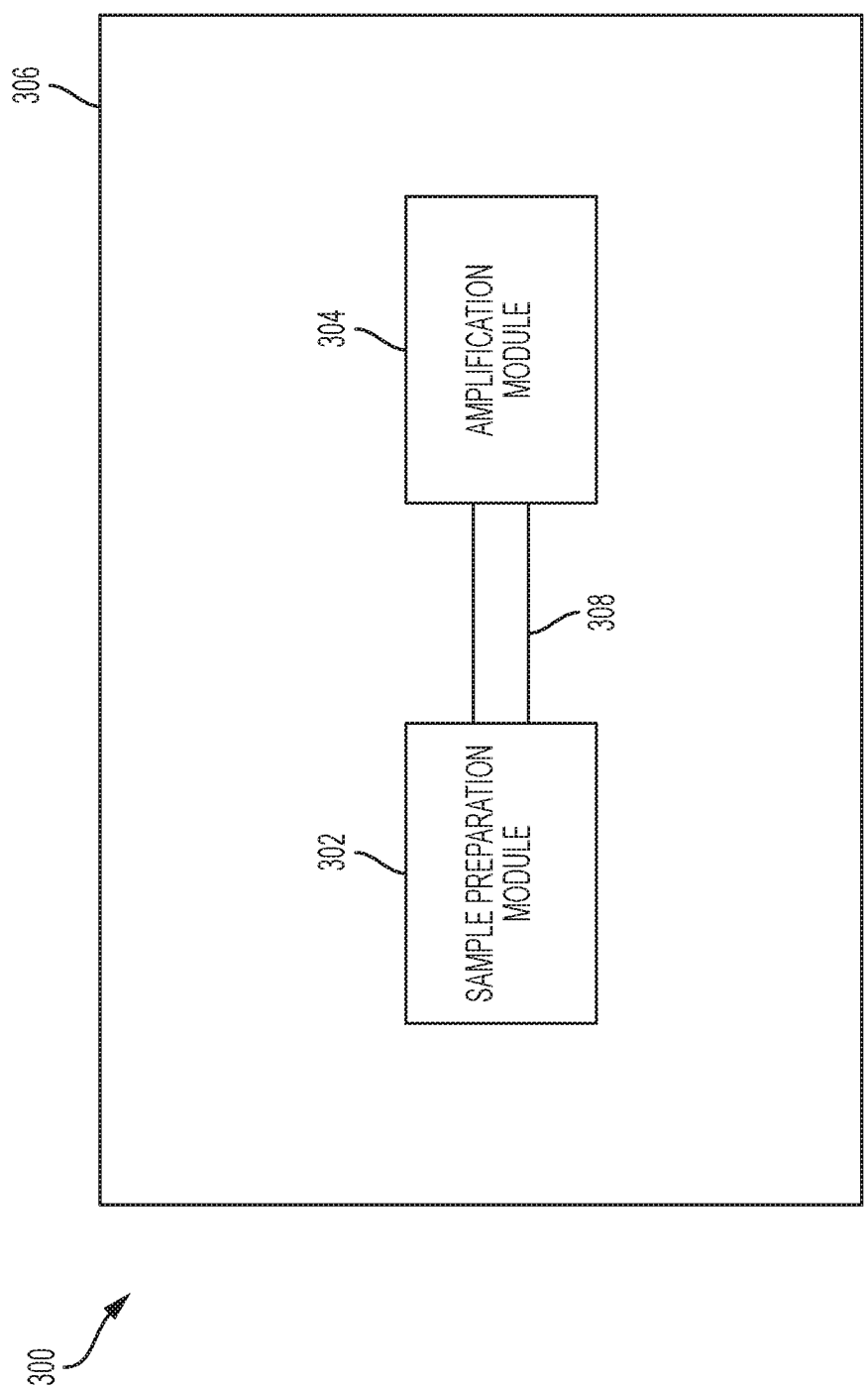
FIG. 3A is a schematic illustration of a sample carrier that includes a sample preparation module and an amplification module on a card, in accordance with an example embodiment.
Figure 3B:
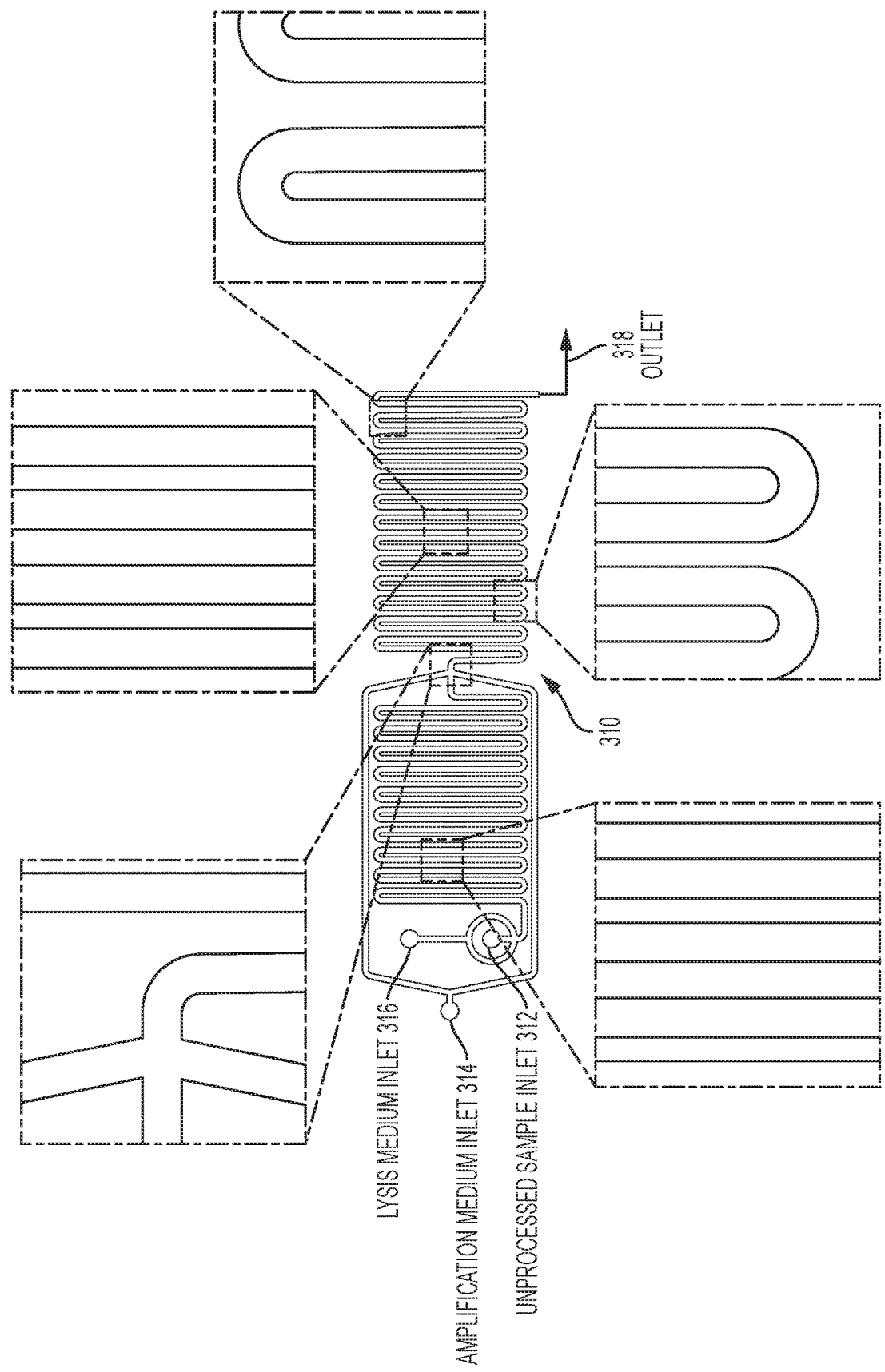
FIG. 3B is an illustration of the microfluidic configuration of the sample preparation module shown in FIG. 3A, in accordance with an example embodiment.

FIG. 3A illustrates another example sample carrier 300. In this example, sample carrier 300 includes a sample preparation module 302 and an amplification module 304 mounted on a card 306 with a tube 308 fluidly coupling the outlet of the sample preparation module 302 to the inlet of the amplification module 304. The card 306 can be similar to card 204 shown in FIG. 2A and described above. The sample preparation module 302 has an unprocessed sample inlet for receiving an unprocessed sample (e.g., a whole blood sample), an amplification medium inlet for receiving a nucleic acid amplification medium (e.g., for LAMP amplification), a lysis medium inlet for receiving a lysis medium, an outlet, and a microfluidic channel that connects the inlets to the outlet. FIG. 3B illustrates an example configuration of the sample preparation module 302 along with images of different portions of the microfluidic channel. As shown in FIG. 3B, sample preparation module 302 includes a serpentine microfluidic channel 310 that fluidly connects the unprocessed sample inlet 312, amplification medium inlet 314, and lysis medium inlet 316 to the outlet 318. In an example embodiment, the microfluidic channel 310 is 10 mm in length, 500 µm in width, and 200 µm in depth. The sample inlet 312 and lysis medium inlet 316 can be connected to the microfluidic channel 310 so that the applied sample and lysis medium flow together through the entire length of the microfluidic channel 310. The amplification medium inlet 314 may be connected to the microfluidic channel 310 so that the applied nucleic amplification medium flows through only a portion of the microfluidic channel 310 (e.g., through the downstream half of the microfluidic channel 310). Example Application 2 discussed below sets forth an example method of fabricating the sample preparation module shown in FIG. 3B.

In an example method of using sample preparation module 302, an unprocessed sample, nucleic acid amplification medium, and lysis medium are applied to their respective inlets, for example, using syringe pumps with controlled flow rates. The unprocessed sample, lysis medium, and nucleic acid amplification medium mix together as they flow through the microfluidic channel toward the outlet. During this flow through the microfluidic channel, the lysis medium lyses cells in the unprocessed sample to provide an amplification-ready processed sample at the outlet. The outlet of the sample preparation module 302 is fluidly connected to the inlet of the amplification module 304 by a tube 308. Thus, the processed sample flows from the outlet of the sample preparation module 302 through the tube 308 and into the amplification module 304 for amplification. In some implementations, after the processed sample fills the amplification module 304, the tube 308 is removed and the amplification module 304 is sealed with a transparent cover.

Sample carrier 300 may also include a data storage portion (not shown), such as a QR code, bar code, magnetic strip, RFID tag or other structure that stores information regarding the sample carrier 300. The information could include, for example, any of the items described above for QR code 206.

Figure 3C:
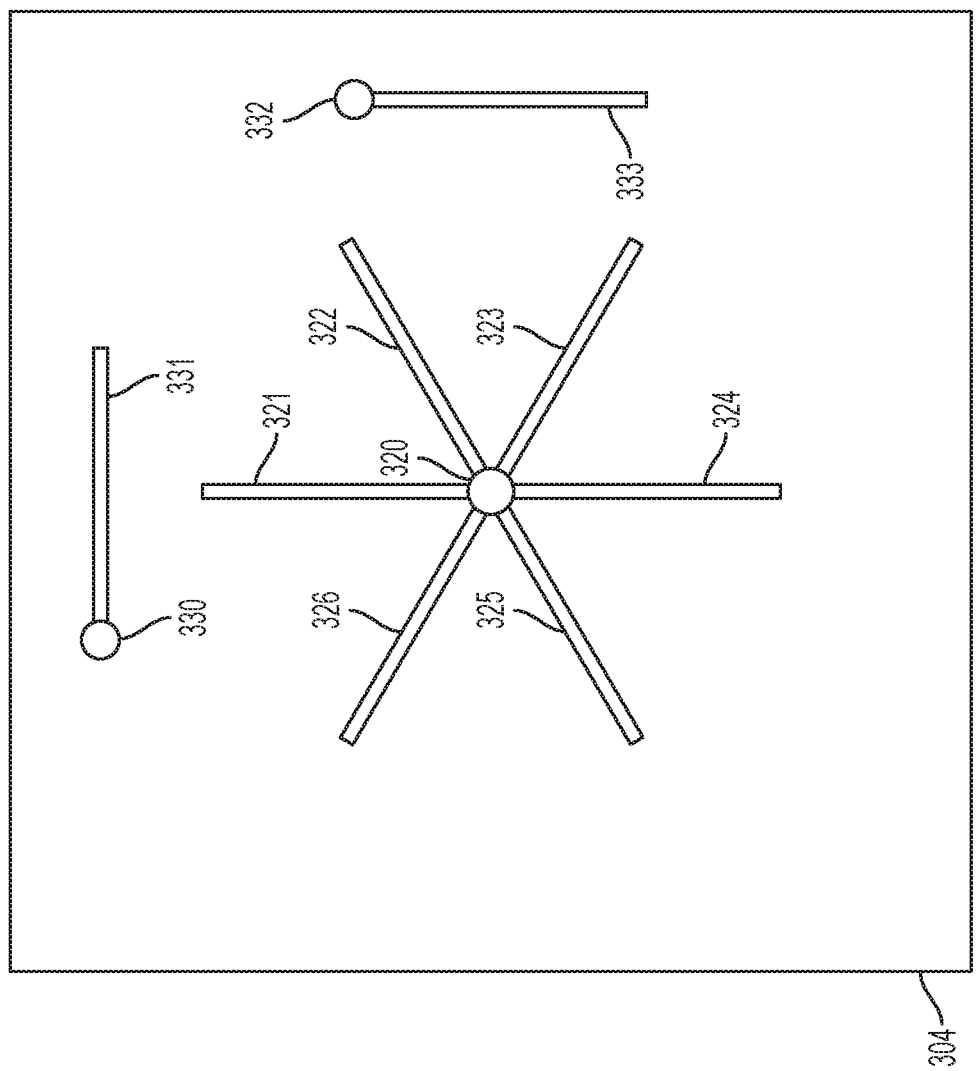
FIG. 3C is a top view of the amplification module shown in FIG. 3A, in accordance with an example embodiment.

FIG. 3C illustrates an example configuration of amplification module 304. In this example, amplification module 304 includes a microfluidic structure that is formed in a silicon chip and sealed by a transparent cover, similar to amplification module 202 shown in FIGS. 2B and 2C and described above, but with a different form factor and arrangement of inlets and microfluidic flow channels. FIG. 3C is a view of the microfluidic structure through the transparent cover. In this example, amplification module 304 is square (29 mm×29 mm) and has a central sample inlet 320 from which six microfluidic flow channels 321-326 extend radially outward. Thus, a sample applied to central sample inlet 320 flows into each of the flow channels 321-326 so as to be evenly distributed therein. Amplification module 304 also has two independent flow channels with respective sample inlets on the periphery, shown in FIG. 3C as sample inlet 330 connected to flow channel 331 and sample inlet 332 connected to flow channel 333. In an example embodiment, the flow channels 321-326, 331, and 333 are 10 mm in length, 500 µm in width, and 200 µm in depth, representing a volume of 1 microliter in each channel, and the sample inlets 320, 330, and 332 are 2 mm in diameter. Primers for amplifying target nucleic acid sequences corresponding to specific pathogens can be deposited in some or all of flow channels 321-326, 331, and 333. In addition, a positive control mixture can be deposited in one or more of flow channels 321-326, 331, and 333 that are intended to serve as positive controls. The positive control mixture can include both a target nucleic acid sequence and a primer configured to amplify that sequence. As well, primers may be omitted from one or more of flow channels 321-326, 331, and 333 that are intended to serve as negative controls. Example Application 2 discussed below sets forth an example method of fabricating the amplification module 304 shown in FIG. 3C.

Figure 4A:
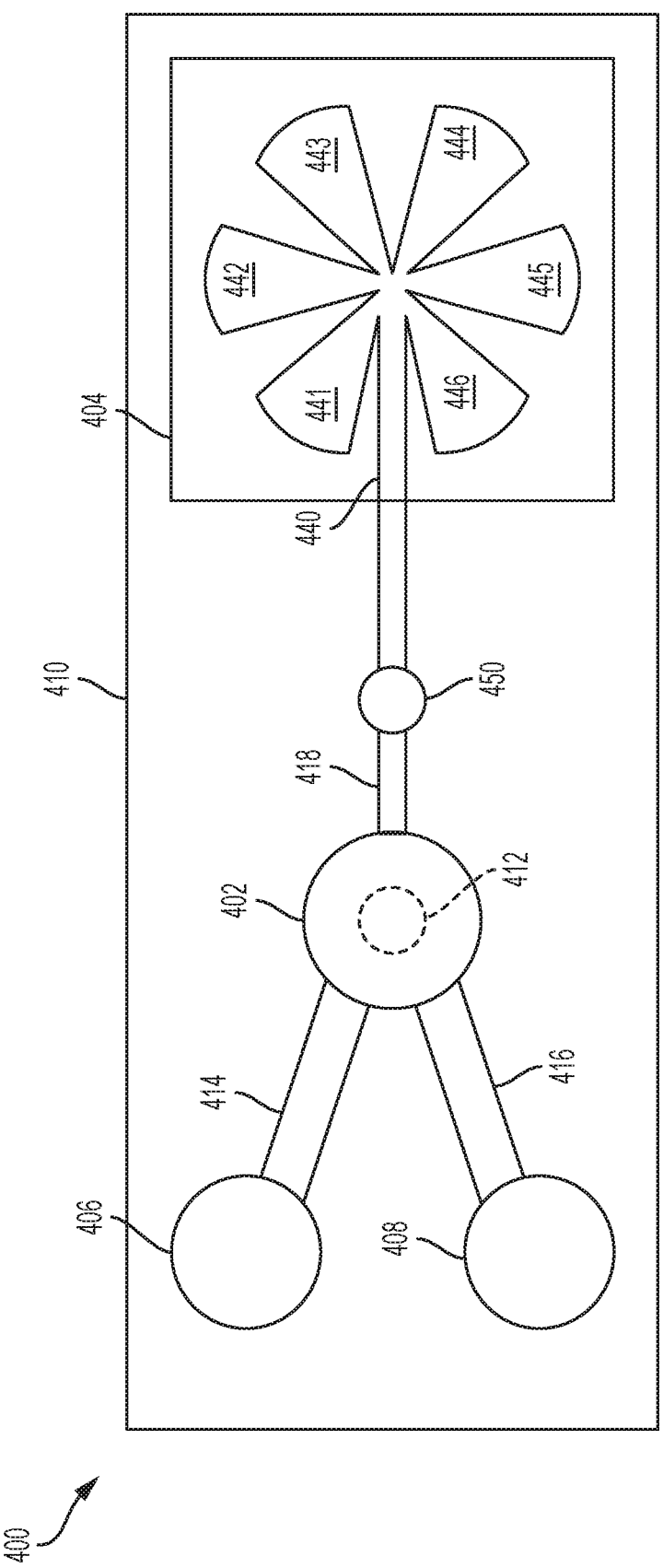
FIG. 4A is a schematic illustration of a sample carrier that includes a sample preparation module, an amplification module, an amplification medium reservoir, and a lysis medium reservoir, in accordance with an example embodiment.

FIG. 4A illustrates another example sample carrier 400. In this example, sample carrier 400 comprises a sample preparation module 402, an amplification module 404, an amplification medium reservoir 406, and a lysis medium reservoir 408, mounted on an acrylic base 410. The sample preparation module 402 has a sample inlet 412 through which a sample (e.g., a droplet of whole blood) can be received. The sample preparation module 402 is fluidly connected to an amplification medium inlet 414, a lysis medium inlet 416, and an outlet 418. The amplification medium reservoir 406 contains a predetermined amount (e.g., 50 microliters) of a nucleic acid amplification medium. The lysis medium reservoir 408 contains a predetermined amount (e.g., 40 microliters) of a lysis medium.

Figure 4B:
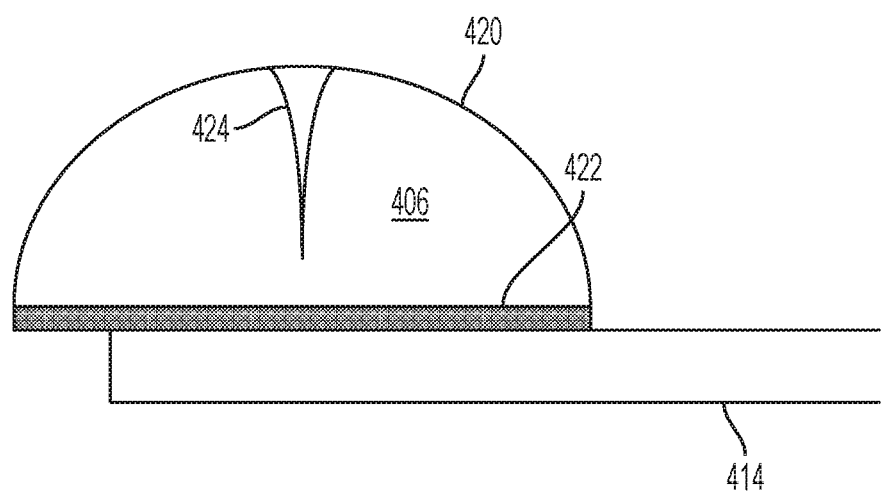
FIG. 4B is a cross-sectional view of the amplification medium reservoir shown in FIG. 4A, in accordance with an example embodiment.

In an example implementation, amplification medium reservoir 406 and the lysis medium reservoir 408 are provided as flexible compartments that can be pressed by the user to move fluids through the sample carrier 400. FIG. 4B is a cross-sectional view that shows an example of such an amplification medium reservoir 406, and FIG. 4C is a cross-sectional view that shows an example of such a lysis medium reservoir 408.

In the example shown in FIG. 4B, the amplification medium reservoir 406 is defined by the space between a convex rubber button 420 that is positioned over a membrane 422. The membrane 422 separates the amplification medium reservoir 406 from the amplification medium inlet 414. A protrusion 424 attached to the convex rubber button 420 extends into the amplification medium reservoir 406. With this configuration, the convex rubber button 420 can be pressed so that the protrusion 424 punctures the membrane 422. Once the membrane 422 is punctured, the nucleic acid amplification medium is able to flow from the amplification medium reservoir 406 into the amplification medium inlet 414 and then into the sample preparation module 402.

Figure 4C:
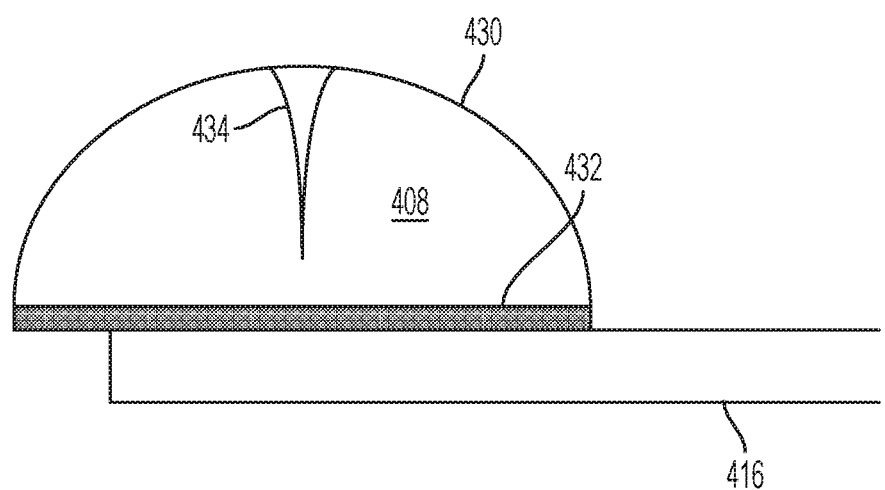
FIG. 4C is a cross-sectional view of the lysis medium reservoir shown in FIG. 4A, in accordance with an example embodiment.

In the example shown in FIG. 4C, the lysis medium reservoir 408 is defined by the space between a convex rubber button 430 that is positioned over a membrane 432. The membrane 432 separates the lysis medium reservoir 408 from the lysis medium inlet 416. A protrusion 434 attached to the convex rubber button 430 extends into the lysis medium reservoir 408. With this configuration, the convex rubber button 430 can be pressed so that the protrusion 434 punctures the membrane 432. Once the membrane 432 is punctured, the lysis medium is able to flow from the lysis medium reservoir 408 into the lysis medium inlet 416 and then into the sample preparation module 402.

The sample preparation module 402 can also be made into a flexible compartment by attaching a convex rubber button over the sample inlet 412 after a sample has been applied to the sample inlet 412.

The amplification module 404 comprises a microfluidic structure in a silicon substrate and enclosed by a transparent cover. The microfluidic structure includes a sample inlet 440 connected to six wedge-shaped microfluidic chambers 441-446. In an example embodiment, the wedge-shaped microfluidic chambers 441-446 are arranged to fill a circle with a diameter of 40 mm, and each of the microfluidic chambers 441-446 has a depth of 200 µm to accommodate a volume of up to 250 microliters. Each of the microfluidic chambers 441-446 has corresponding vent holes in the transparent cover. In an example implementation, four of the microfluidic chambers have disposed therein primers configured to amplify one or more target nucleic acid sequences of specific pathogens, one of the microfluidic chambers has disposed therein a positive control mixture (e.g., primers along with their corresponding target nucleic acid sequence) so as to serve as a positive control, and one of the microfluidic chambers has no primers so as to serve as a negative control. The primers can be printed in their respective chambers with a piezoelectric noncontact printer (GeSim Nanoplotter with Nano-Tip A-J), using a series of 0.25 nL droplets distributed over the bottom surface of the chambers, and then dried.

The outlet 418 of the sample preparation module 402 is fluidly connected to the sample inlet 440 of the amplification module 404 via a plug 450 that has functions as a valve. In an example embodiment, plug 450 is a cylinder of silicon material with an axis generally perpendicular to the acrylic base 410 and a pass-through hole extending through the plug 450 perpendicular to the axis. The plug 450 can move up and down in sample carrier 400 to control fluid flow through the outlet 418. For example, in an upper position, the plug 450 may block fluid flow through the outlet 418, and, in a lower position, the pass-through hole may be aligned with the outlet 418 so as to allow fluid flow.

Figure 4D:
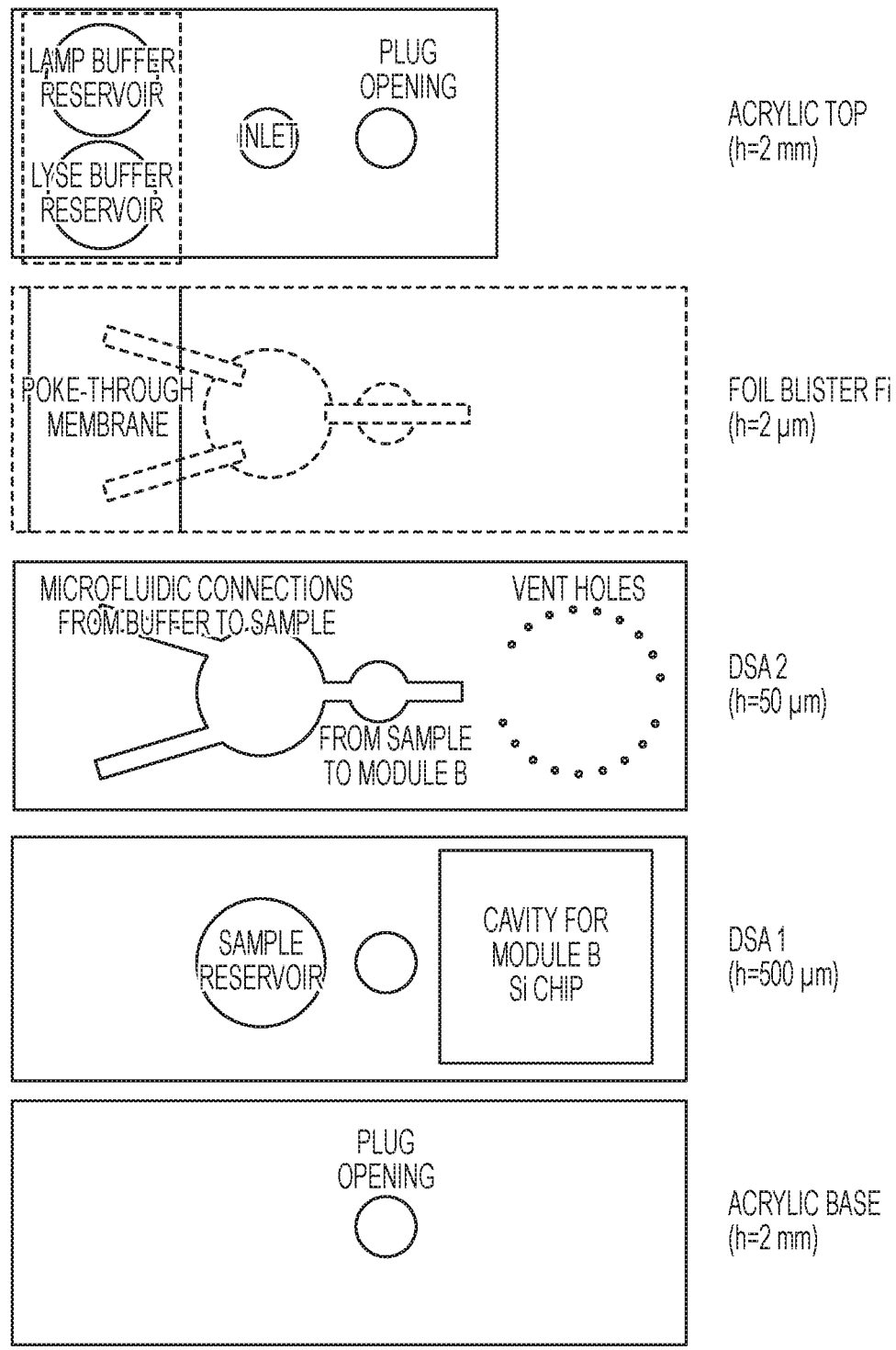
FIG. 4D illustrates the individual layers in the sample carrier shown in FIG. 4A, in accordance with an example embodiment.

FIG. 4D illustrates an example set of layers that may be laminated together to form the sample carrier 400. In this example, the bottom layer is an acrylic base layer (2 mm thick) with an opening to accommodate plug 450. The next layer above is a first layer of double-sided adhesive (500 µm thick) that has openings for the sample preparation chamber 402, for the plug 450, and for the amplification module 404. The next layer above is a second layer of double-sided adhesive (50 µm thick) that has interconnected pattern of openings for the sample preparation chamber 402 and the plug 450 and openings that define the amplification medium inlet 414, the lysis medium inlet 416, and outlet 418. The second layer of double-sided adhesive also has openings that serve as vent holes for the microfluidic chambers 441-446. The next layer above is a layer of foil (2 µm thick) that serves as the puncturable membranes 422 and 432 described above. The next layer above is an acrylic top layer (2 mm thick) with openings for the amplification reservoir 406, lysis medium reservoir 408, sample inlet 412, and plug 450. Convex rubber buttons (e.g., as shown in FIGS. 4B and 4C) can be attached to the acrylic top layer over the openings for the amplification reservoir 406 and lysis medium reservoir 408. A convex rubber button can also be attached to the acrylic top layer over the sample inlet 412 after a sample has been applied. The openings in the acrylic base layer, double-sided adhesive layers, and acrylic top layer could be formed by loser cutting or other means.

The sample carrier 400 can be used as follows. A user obtains a sample of whole blood (e.g., a 10 microliter droplet) by a fingerstick or other means and applies the blood sample to the sample inlet 412. The user then seals the sample inlet 412 by covering it with an adhesive-backed cover with a convex rubber button. The user then presses the convex rubber button 430 of the lysis medium reservoir 408 so as to puncture the membrane 432. This causes the lysis medium contained in the lysis medium reservoir 408 to flow into the lysis medium inlet 408 and then into the sample preparation module 412 to mix with the sample. Diffusion mixing will occur, with lysis completion occurring within a few minutes. Lysis completion can be visually observed when the initially red solution turns clear due to the degradation of the red blood cell outer membranes.

After lysis completion, the user presses the convex rubber button 420 of the amplification medium reservoir 406 so as to puncture the membrane 422. This causes the nucleic acid amplification medium contained in the amplification medium reservoir to flow into the amplification medium inlet 414 and then into the sample preparation module 402 to mix with the processed (chemically lysed) sample. To transfer this mixture of processed sample and amplification medium from the sample preparation module 402 to the amplification module 404, the user moves the plug 450 (e.g., by pressing) to a position that allows fluid flow through outlet 418 and then presses on the convex rubber button covering the sample inlet 412 to apply pressure to the sample preparation chamber 402. The applied pressure moves the fluid contents of the sample preparation chamber 402 through the outlet 418 and into the sample inlet 440 of the amplification module 404. From the sample inlet 440, the mixture of processed sample and amplification medium moves into the microfluidic chambers 441-446 so as to be evenly distributed therein. The vent holes at the distal ends of the microfluidic chambers enable gas to escape, so that the microfluidic chambers can be filled completely without bubbles. At this stage, the sample carrier 400 is ready to be placed into the detection instrument 104 for measurement.

4. Example Detection Instrument

Figure 5B:
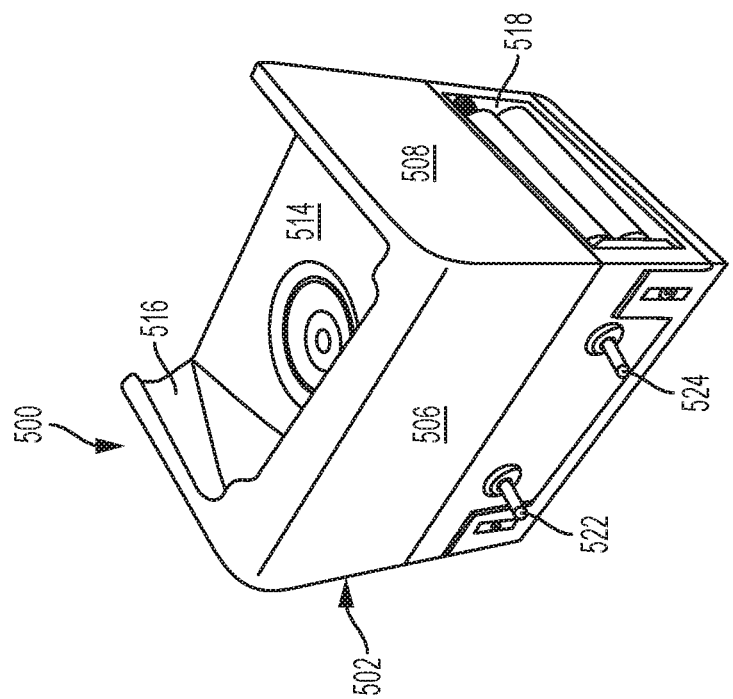
FIG. 5B is an exterior view of the detection instrument shown in FIG. 5A that shows the back side and left side thereof, in accordance with an example embodiment.
Figure 5A:
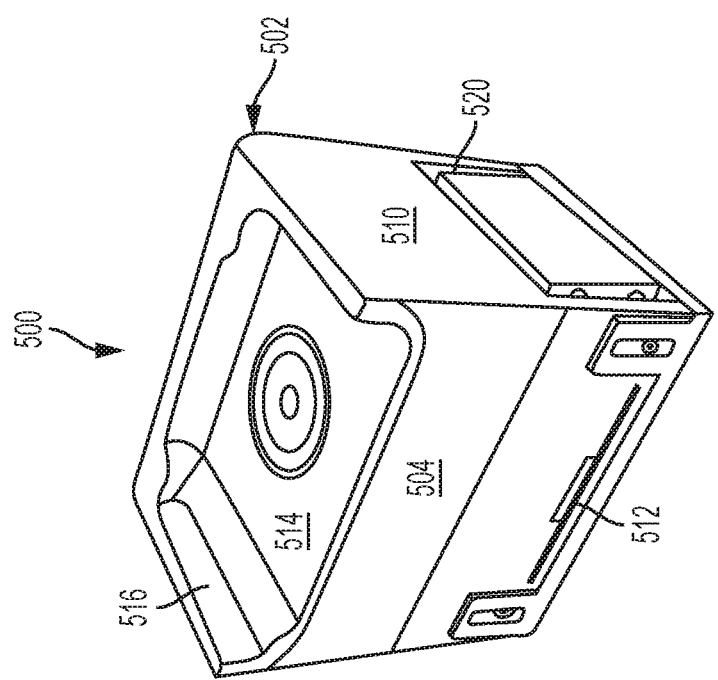
FIG. 5A is an exterior view of a detection instrument that shows the front side and right side thereof, in accordance with an example embodiment.

FIGS. 5A and 5B are exterior views of an example detection instrument 500. In this example, the detection instrument 500 has a housing 502 with a front side 504, a back side 506, a left side 508, and a right side 510. The front side 504 of detection instrument 500 has a slot 512 through which a sample carrier can be inserted. The top of detection instrument 500 has a mounting surface 514 and sidewalls 516 that define a mounting slot into which a mobile computing device (e.g., a smartphone) can be inserted from the front. Battery compartments 518 and 520 are provided in the left side 508 and right side 510, respectively. Switches 522 and 524 are disposed on the back side 506.

Figure 6:
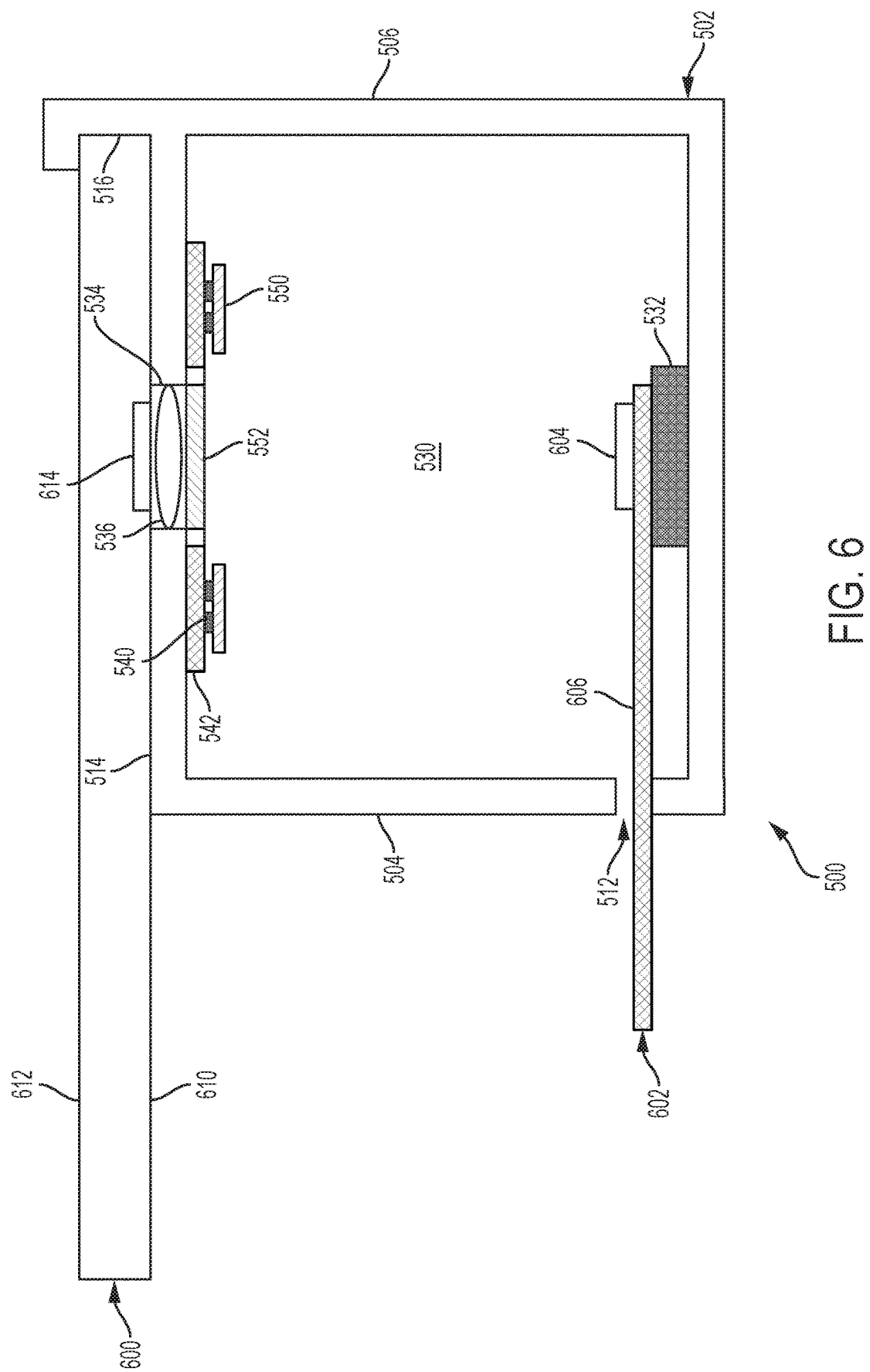
FIG. 6 is a schematic cross-sectional view of the detection instrument shown in FIGS. 5A and 5B with a smartphone mounted thereto and a sample carrier inserted therein, in accordance with an example embodiment.

The internal components of detection instrument 500 are shown in FIG. 6, which is a cross-sectional view in a plane parallel to right side 510 cutting through front side 504 and back side 506. For purposes of illustration, FIG. 6 shows the detection instrument 500 with a smartphone 600 mounted thereto and a sample carrier 602 inserted into slot 512. Sample carrier 602 could be configured like sample carrier 200, sample carrier 300, sample carrier 400, or could be configured in some other way. For purposes of illustration, sample carrier 602 is shown with an amplification module 604 mounted to a card 606. It is to be understood, however, that sample carrier 602 could also include a sample preparation module, a QR code (or other data storage), a lysis medium reservoir, an amplification medium reservoir, and/or other components as described above for sample carrier 200, sample carrier 300, or sample carrier 400.

As shown in FIG. 6, the housing 502 encloses an exterior space 530 in which the amplification module 604 is disposed in a working position. In this working position, a portion of sample carrier 602 extends out of slot 512, and the amplification module 604 is able to interact with the optical and thermal components of detection instrument 500). In this regard, detection instrument 500 includes a heating device 532 coupled to the bottom portion of the housing 502. In the working position shown in FIG. 6, the amplification module 604 is above and in thermal contact with the heating device 532 through the card 606. The heating device 532 is configured to control the temperature within the microfluidic chambers of amplification module 604 based on the type of nucleic acid amplification to be performed. For PCR-based nucleic acid amplification, the heating device 532 may be configured to perform temperature cycling. For LAMP-based nucleic acid amplification, the heating device 532 may be configured to maintain a predetermined temperature within the microfluidic chambers.

In one example, the heating device 532 comprises a positive temperature coefficient (PTC) heater that allows a stable temperature to be maintained for LAMP-based nucleic acid amplification without an external temperature controller. The PTC heater is made from a ceramic material that functions as a self-regulating heating element. When the temperature of the PTC heating element increases, the electrical resistance increases nonlinearly, resulting in decreased heat output to set the temperature at a predesigned limit. The PTC heater can be used without an over-temperature protector, while providing uniform heating, low-voltage operation, and light weight. A suitable PTC heater is available from Uxcell. Hong Kong, China (12V-80° C. model). To set the temperature of the amplification module 604 to about 64 to 66° C. for 60 minutes to perform LAMP-based nucleic acid amplification, this PTC heater can be powered by a standard 9 V battery placed in battery compartment 520. Switch 522 can be used to turn the heating device 532 on and off.

Smartphone 600 is mounted to detection instrument 500 such that the back side 610 of smartphone 600 is supporting by the mounting surface 514 at the top of housing 504 and the front side 612 of smartphone 600 (which may include a display, touchscreen, and other controls) is accessible. The mounting surface 514 has an opening 534 in which a macro lens 536 is disposed. The smartphone 600 is mounted to the mounting surface 514 such that a rear-facing camera 614 of the smartphone 600K is positioned over the opening 534 and optically coupled to the macro lens 536. In one example, the camera 614 has 13 megapixels, with a pixel size of 1.4 μm. The macro lens 536 is positioned over the heating device 532 where the amplification module 604 is disposed in the working position such that the amplification module 604 is in the field of view of camera 614. The macro lens 536 in front of camera 614 enables close-up photography of the amplification module 604 at a reduced distance (e.g., 50 mm), while keeping the field of view large enough (e.g., 24×24 mm) to encompass all of the microfluidic chambers with only negligible barrel distortion. In one example, macro lens 536 is a 12.5× macro lens available from TECHO.

The camera 614 can be controlled by software in the smartphone 600 to capture multiple images of the amplification module 604 as nucleic acid amplification is occurring in the microfluidic chambers. For example, the camera 614 could be controlled to capture images at one-minute intervals. The extent of nucleic acid amplification in each microfluidic chamber can be monitored by a fluorophore (e.g., an intercalating dye) in the nucleic acid amplification medium that fluoresces when incorporated in amplified nucleic acid. The fluorescence light from the fluorophore in each microfluidic chamber can be observed in the images captured by the camera 614.

Figure 7:
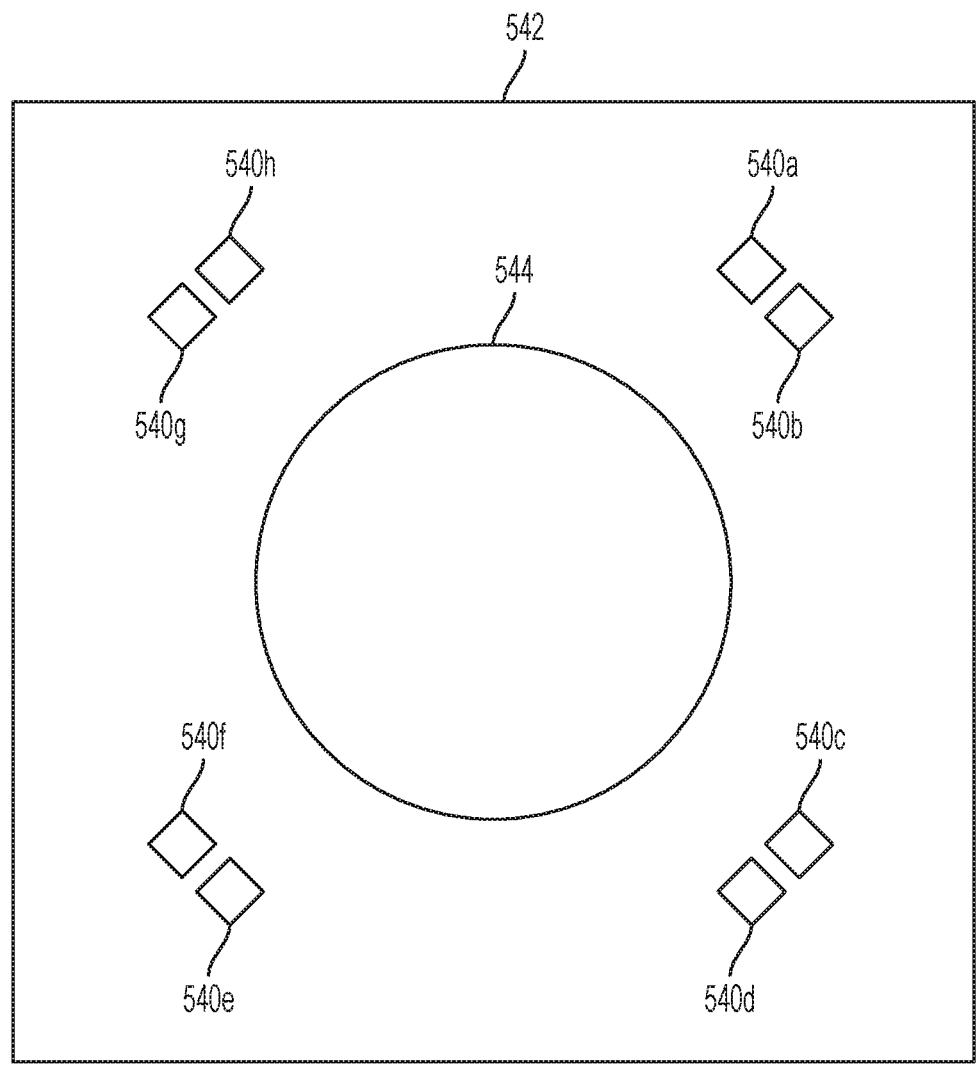
FIG. 7 is a top view of an arrangement of light emitting diodes (LEDs) on a printed circuit board (PCB) that is included in the detection instrument shown in FIG. 6, in accordance with an example embodiment.

To excite the fluorophore, the detection instrument 500 can include a plurality of light sources 540 that emit excitation light, and the fluorophore (when incorporated in amplified nucleic acid) emits the fluorescence light in response to the excitation light. As shown in FIG. 6, the light sources 540 are mounted on a printed circuit board (PCB) 542 that is attached to housing 502. The light sources 540 can be light-emitting diodes (LEDs) that are mounted on PCB 542 so as to be symmetrically arranged around the macro lens 536. For example, FIG. 7 illustrates an arrangement of eight LEDs 540a-h mounted on PCB 542 in four pairs in a symmetrical arrangement around a central aperture 544. The central aperture 544 is aligned with the macro lens 536 and camera 614. This symmetrical arrangement beneficially enables the light from the light source 540 to overlap at the amplification module 604 and provide a substantially uniform intensity distribution of the excitation light illuminating the plurality of microfluidic chambers in the amplification module 604. For example, ray-tracing software (Zemax) may be used to design the arrangement of LEDs to provide an intensity variation that is less than 2% over the active area of the amplification module 604.

To excite fluorescence of EvaGreen intercalating dye as the fluorophore, the LEDs can be blue LEDs, such as XPEBBL high-power LEDs available from Cree, Inc. ($\lambda_{peak}$=485 nm, viewing angle=135°, 45 lumens/watt). The LEDs in this example can be powered by two 1.5 V (size AAA) batteries placed in battery compartment 518. The LEDs can be turned on and off using switch 524. It is to be understood that other types of LEDs that emit light with other wavelengths could be used to excite fluorophores. Further, the LEDs could be arranged differently than shown in FIG. 7, and a greater or fewer number of LEDs could be used.

Preferably, the housing 502 is designed to block out external light, so that most of the light detected by the camera 614 is fluorescence light from the fluorophore. Further, to minimize the mount of excitation light detected by the camera 614, the light sources 540 can be covered by shortpass filters 550 (e.g., with a shortpass filter covering each pair of LEDs shown in FIG. 7) and the macro lens 536 can be covered by a longpass filter 552. The shortpass filters 550 pass wavelengths corresponding to the excitation light and block wavelengths corresponding to the fluorescence light, wherein the longpass filter 552 passes wavelengths corresponding to the fluorescence light and blocks wavelengths corresponding to the excitation light. For example, the shortpass filters 550 can have a cut-off wavelength of 490 nm (e.g., model ZVS0510 available from Asahi Spectra Torrance, Calif.) and the longpass filter 552 can have a cut-off wavelength of 525 nm (e.g., model 84-744 available from Edmund Optics, Barrington, N.J.).

The detection instrument 500 shown in FIG. 6 can be used with smartphone 600 and sample carrier 602 as follows. A sample of whole blood (e.g., from a finger prick) is applied to a sample inlet port on the sample carrier 602 and mixed with a lysis medium and nucleic acid amplification medium, which could, for example, be applied from reservoirs in the sample carrier 602. Cell lysis is allowed to progress to completion, and the mixture is then loaded into the amplification module 604. The amplification module 604 includes microfluidic chambers that are pre-loaded with primers to detect one or more target nucleic acid sequences corresponding to one or more pathogens. The amplification module 604 is then sealed with a transparent cover (i.e., transparent to the excitation light and the fluorescence light), and the sample carrier 602 is inserted into the detection instrument 500 through slot 512 such that the amplification module 604 is in the working position over the heating device 532, as shown in FIG. 6. The smartphone 600 is attached to the top of the detection instrument 500 such that the amplification module 604 is focused in the field of view of the camera 614 via the macro lens 536. The switch 522 is turned on to turn on the heating device 532 to incubate the amplification module 604 for nucleic acid amplification. The switch 524 is turned on to turn on the light sources 540 to illuminate the amplification module 604 with excitation light. The camera 614 captures multiple images during the amplification process (e.g., at one-minute intervals). The images can be displayed on the display screen of the smartphone 600. The lighting up of a particular microfluidic chamber in the images indicates the presence of the corresponding pathogen in the blood sample. The smartphone 600 could be programmed to do additional processing of the images to provide the result, or the smartphone 600 could communicate with an external, cloud-based computing system to process image data.

5. Example Computing Device

Figure 8:
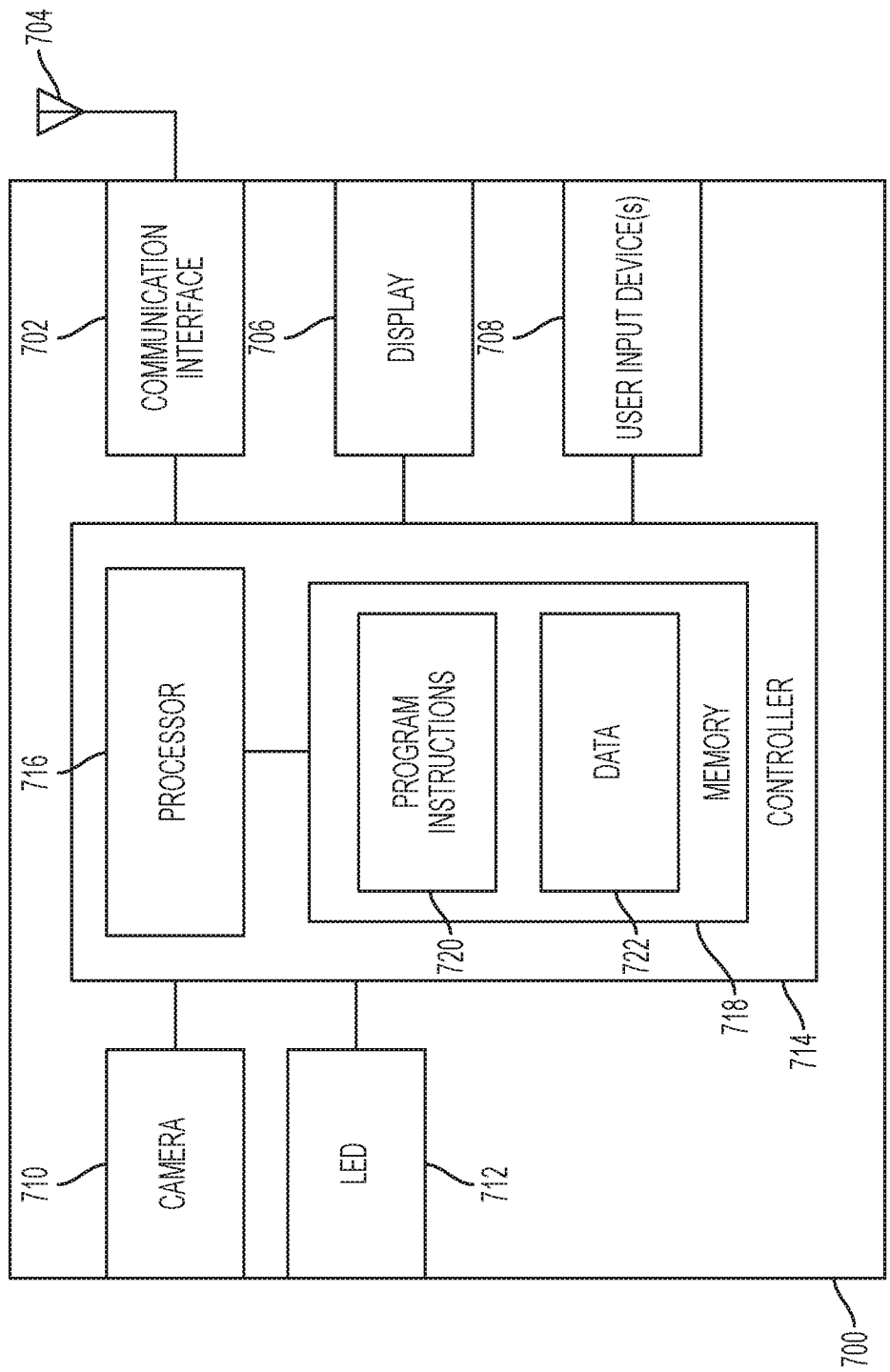
FIG. 8 is a block diagram of an example mobile computing device, in accordance with an example embodiment.

FIG. 8 is a block diagram illustrating an example mobile computing device 700. The mobile computing device 700 could be a smartphone, a handheld computer, a tablet computer, or other portable computing device. For example, mobile computing device 700 could correspond to computing device 106 shown in FIG. 1 or smartphone 600 shown in FIG. 6.

The mobile computing device 700 includes a communication interface 702 for wireless communication via an antenna 704. The wireless communication could involve sending or receiving voice, images, video, data, or other information. The wireless communication could use any type of wireless communication protocol, such as 3G or 4G cellular communication protocols, WiFi, or Bluetooth. Instead of or in addition to communication interface 702, the mobile computing device 700 may include a communication interface for communicating over USB, Ethernet, or other wired connections.

The mobile computing device 700 also includes a display 706 and one or more user input device(s) 708. The display 706 can display text, images, graphics, or other visual information. The user may enter input (e.g., information, commands, etc.) or otherwise interact with the mobile computing device 700 via the user input device(s) 708. In one example, the user input device(s) 708 may include a touchscreen over the display 706. Alternatively or additionally, the user input device(s) 708 may include a keypad, buttons, or other controls.

The mobile computing device 700 is able to capture still images and/or video images through the use of a camera 710. The camera 710 includes a lens and an image sensor, such as a CCD. The camera 710 could be on a side of the mobile computing device 700 that is opposite the side that includes the display 706. The mobile computing device 700 may also include a light source, such as a white-light LED 712, next to the camera 710. The LED 712 may be intended for flash photography, for example.

The mobile computing device 700 may be controlled by a controller 714 that includes a processor 716 and a memory 718. The memory 718 could include random access memory (RAM), read-only memory (ROM), flash memory, or any other type of non-transitory media. The memory 718 may store program instructions 720 and data 722. The processor 716 may execute the program instructions 720 to cause the mobile computing device 700 to perform operations, which could include any of the operations described herein. The operations may involve communicating via the communication interface 702, displaying output on display 706, receiving user input via user input device(s) 708, using camera 710 to obtain images (still images or video), and/or controlling the illumination of LED 712. In some examples, the program instructions 720 may include software for one or more applications (often known as "Apps") that can be accessed by a user.

In one example, mobile computing device 700 may be programmed to provide a detection user interface (DUI) for using the device 700 with a detection instrument and sample carrier (e.g., as shown in FIG. 6) to perform an assay that can detect one or more pathogens in a sample (e.g., a sample of whole blood). The DUI can provide graphical/written instructions (e.g., on display 706) for performing the assay, control the data collection during imaging of the amplification module, gather information from the user, and transmit measurements to a cloud-based data management system (e.g., server 110). The DUI may prompt the user to use the mobile computing device 700 to record a barcode or QR code on the sample carrier (which could identify the pathogen test within each microfluidic chamber and/or include other information). The DUI may also prompt the user to record information about the user (e.g., a User ID and password), the patient (e.g., name, age, sex), the sample origin (e.g., blood, serum, mucus swab, saliva, etc.), the test (e.g., date, location), and/or other information. Based upon the input information read from the barcode/QR code and provided by the user, the DUI will provide graphical/text instructions (e.g., on display 706) for performing all assay steps. For example, the DUI may provide instructions for obtaining a sample (e.g., by a finger prick), applying the sample to the sample carrier, pressing buttons on the sample carrier to apply lysis buffer and nucleic acid buffer, inserting the sample carrier into the detection instrument, connecting the smartphone, and starting the detection sequence. The DUI will record the sequence of fluorescence images of each video frame during the scan, and (in the background) analyze the images to determine qualitatively whether each tested pathogen is present or undetectable in the sample and/or provided a quantitative measure of the concentration of each tested pathogen in the sample. The DUI can utilize the positive and negative controls in the amplification module to perform error analysis by determining if the control values fall within acceptable bounds for a valid test. The DUI can also wirelessly transmit test information and all user/patient information to a cloud-based data management system (e.g., server 110).

6. Example Cloud-Based Data Management System

The incorporation of a smartphone in the detection platform not only reduces the cost of the detection system but also enables streamlined integration of the sensing function with a network for infectious disease epidemiology. Many users (e.g., physicians, public health officials, etc.) may not only interested in the results of tests that they conduct themselves, but also in the results of a network of similar users who perform testing on geographically distributed patients. The detection results can be collected by the DUI described above and transmitted through a data network to one or more servers (e.g., server 110 shown in FIG. 1) for the reporting of the pathogens or further analysis at centralized laboratories, interpretation by remote physicians, or by physicians interested in epidemiological trends. Due to the portability of the smartphone-based system, the detection can be quickly deployed and performed in a wide range of regions upon the outbreaks of infectious diseases, especially in resource-poor environments.

Figure 9:
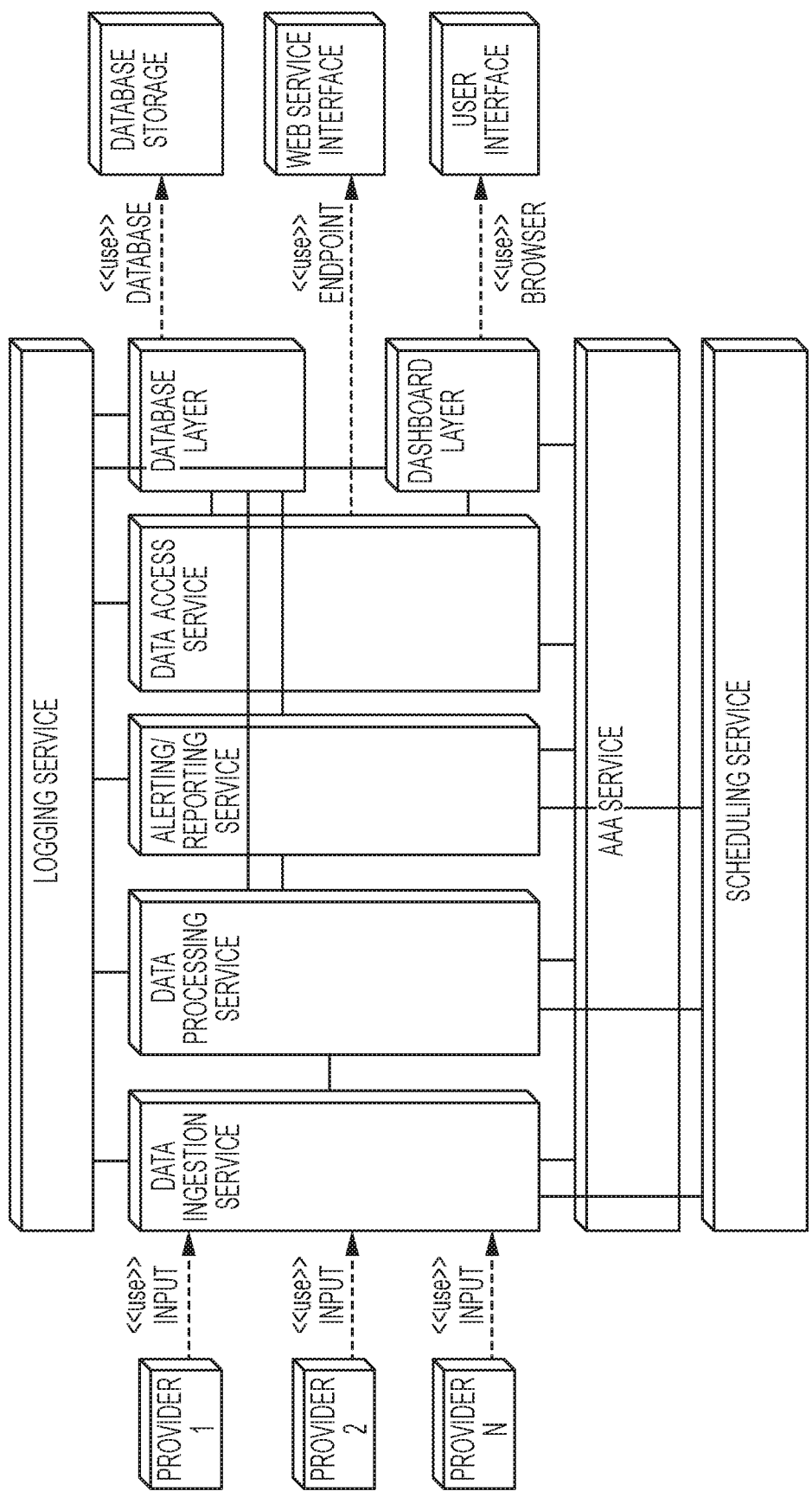
FIG. 9 schematically illustrates an architecture of a cloud-based data management system, in accordance with an example embodiment.

The data collected from the tests can be stored, managed, and made available for use through a cloud-based data management system. FIG. 9 schematically illustrates an example architecture for such a cloud-based data management system. The data ingestion service enables smartphones that perform the tests to communicate with the cloud-based system, for example, to report positive and negative test results, as well as the location, time, and other information associated with the tests (e.g., the serial number or other identifier of the sample carrier used). The data processing service can aggregate this information, and the data access service can make at least some of the aggregated information available to authorized users. For example, a web-based interface or other type of user interface to the cloud-based system may provide a data visualization tool that enables authorized users to select, prioritize, and view the results of tests performed by other users. For example, a user may specify the particular test results to be viewed on the basis of location, disease, pathogen, patient type, or other criteria. The alert/reporting service enables direct messaging of test results or trends to interested users. For example, a user may request to receive an alert when positive results for specific diseases in specific locations are reported.

7. Example Application 1: Detection of Equine Infectious Respiratory Diseases

The smartphone-based system shown in FIGS. 5A, 5B, and 6 and described above was validated using a sample carrier shown in FIGS. 2A, 2B, and 2C to detect the equine infectious respiratory diseases S. Equi, S. Zoo, EHV-1, and EHV-4.

a. Materials and Methods

Amplification modules as shown in FIGS. 2B and 2C were fabricated as follows. A 4-inch <100> silicon wafer (University Wafer, South Boston, Mass.) with one side polished was thoroughly cleaned and used as the substrate in the photolithography process. Positive photoresist SPR 220 (MicroChem, Newton, Mass.) was spin-coated on the polished side of the wafer to form a 4.5 μm covering layer, followed by a soft-bake at 60° C. for 2 min and 110° C. for 1 min. The photoresist was then exposed with an i-line (365 nm) mask aligner (EVG 620) with an expose dose of 180 J/cm$^2$. The exposed regions of the photoresist with the outline of the microfluidic pattern were subsequently removed by immersing the wafer in AZ developer diluted 1:4 with deionized (D) water for about 4 minutes. The photoresist in the unexposed regions was solidified though a hard-bake at 110° C. for 1 min. For anisotropic etching of the silicon substrate, a Bosch process with alternating steps of $SF_6/O_2$ etching and $C_4F_8$ passivation was used to create 200 μm deep trenches in an inductively coupled plasma reactive ion etcher (ICP-RIE). After the etching, the remaining photoresist was stripped with acetone and $O_2$ plasma cleaning, leaving the bare silicon exposed. Because bare silicon has been reported to have inhibitory effects on nucleic acid amplification due to absorption of polymerase, the silicon wafer was thermally oxidized in a furnace (1150° C.) for 2 hours to grow a 200 nm film of $SiO_2$. The wafer was then diced into individual amplification module chips.

The primers were uniformly deposited onto the surfaces of the flow channels before sample loading through pipet injection at the end of each channel (i.e., the portion of the channel farthest away from the sample inlet). Channel 1 serves as the positive control by depositing a mixture of the primer set and template DNAs for S. Zoo, while channel 2 serves as the negative control because no primers are deposited within it. The remaining eight channels were divided into four groups to allow for the deposition of four types of primer sets used in these experiments, with channels 3 and 4 prepared with primers for the S. Equi assay, channels 5 and 6 deposited with primers for the S. Zoo assay, channels 7 and 8 deposited with primers for the EHV-1 assay, and channels 9 and 10 deposited with primers for the EHV-4 assay. The primer solutions injected into the eight channels were prepared with a direct 20-fold dilution of the corresponding primer solution (originally at 55 μM) in nuclease-free water, resulting in a final primer concentration of 2.75 μM. For the solution injected in the positive control channel, 1 μL of the S. Zoo DNA sample solution at a concentration of 5×10⁶ copies/mL is mixed with 1 µL of 20 times diluted 55 µM S. Zoo primer solution to make a 2 µL final solution. After the solutions were prepared, a volume of 1 µL of each solution was taken by a pipet and injected into the corresponding flow channels from the end of each channel. The injected liquids can reach the opposite ends of the flow channels without entering the sample inlet due to their volumes, and all the primers completely dry on the channel surface at room temperature within a few minutes. The primer deposition process enables batches of chips to be prepared in advance and stored for later use. The specific primers that were used for S. Equi, S. Zoo, EHV-1, and EHV-4 are identified below in Table 1.

ATCC, Manassas, Va.), EHV-1 (040-EDV; USDA, Champaign, Ill.), and EHV-4 (044-EDV; USDA, Champaign, Ill.) were chosen as the pathogens due to their widespread virulence among horse populations. The S. Equi and S. Zoo bacteria were received in lyophilized form and propagated in bovine-brain heart infusion medium (Sigma-Aldrich, St. Louis, Mo.) for a period of 16 hours to obtain a carrying concentration of 1×10⁸ colony forming units (CFU)/mL. Glycerol stocks were prepared from this concentration and stored at −80° C. until experiments. The EHV-1 and EHV-4 stock was aliquoted into smaller volumes and also stored at −80° C. until experiments. DNA from all the pathogens was extracted via a standard heat-lysing protocol. The extracted

TABLE 1

| Pathogens | LAMP assay primer sequences |
|---|---|
| Streptococcus Equi | F3: AAA ACT AAG TGC CGG TGC<br>B3: GAG GCG CCT TTT AGA AGA<br>FIP: TAC GAC TAA CCT CAG AGT TCG CTA TCA GTA TTA<br>BIP: CGA CTC CAA GAT TAT CGC GTG ATT GAA CTT TTT<br>Loop F: ACA GTT GTC CCT CCC AAC A<br>Loop B: GCG ATA TAG CCA TAA GTG GAG ATG<br>F: CGG ATA CGG TGA TGT TAA AGA<br>R: TTC CTT CCT CAA AGC CAG A |
| Streptococcus Zooepidemicus | F3: AAA GAC CCT CAT GGG AAA T<br>B3: CCT TAG TTG CCG CAT AGG<br>FIP: CCT GAC TAA CCA AAT ATA AGC CCT TGA GCT GGA<br>BIP: TGT TTG ACG TAT TTT GGT TGC TCT TCT GAG CCT TCT<br>Loop B: GGT GTC ATT ATT AAC ATG GCC TCT<br>F: CAG CAT TCC TGC TGA CAT TCG TCA GG<br>R: CTG ACC AGC CTT ATT CAC AAC CAG CC |
| Equine Herpesvirus 4 | F3: CAA GAC GTA ACA ACG GGA GT<br>B3: CGC AAG TAA CGG CGA TGA<br>FIP: CGC TCT CCG TTT TCT TCC GAC AAG CCA CCC AGG<br>BIP: TTA CCC GGA CGG CCT TCC AAC GGG CAT GTC CTC<br>Loop F: GCC TGC TAC TCC GCA TG<br>Loop B: AGC GTT GTA TAT GAT GCA TCC CCT<br>F: GAC CTC TCC GTT CAC CCA AG<br>R: TCC GTT TTC TTC CGA CAG GG |
| Equine Herpesvirus 1 | F3: GGC ATT TAC GTG TGG TCC TT<br>B3: TCG CGG GCA TTT TTG TAC C<br>FIP: GTC CAG CAA CGG TGC GTT GTG GCA CGC TCG TTA<br>BIP: CGA GCC TGA AGG GGG AAA ACT GGA GCT GTG TGG<br>Loop F: AGG TTG AGA CGG TAA CGC TG<br>Loop B: CAC GTG CGT CGT CGC AA<br>F: GCG CCA GCT GTT TAA CCT TC<br>R: CGG GCA TTT TTG TAC CAC CG |

The silicon chip is covered with a transparent double-sided adhesive (DSA) (ARseal™ 90880, Adhesives Research) with laser-machined holes after the deposition of primers into the channels. The holes are cut to match the position of inlets and ends of the channels at the substrate, to allow for displaced air venting during injection of the test sample. The DSA forms a barrier to evaporation or cross-contamination, and it is compatible with the reagents used in the amplification reaction. After the reaction solution is injected into the channels, the chip is sealed with a glass coverslip (GOLD SEAL® 63760-01, Electron Microscopy Sciences) by peeling off the top covering layer of DSA and binding it with the coverslip. The binding is robust enough to effectively prevent the entrance of air into the flow channels from the surrounding environment. Moreover, the seal provided by the glass coverslip and DSA prevents evaporation of the reaction solution in the flow channels during the heating that is used for nucleic acid amplification.

In these example LAMP assays, S. Equi (ATCC® 9528™; ATCC, Manassas, Va.), S. Zoo (ATCC® 39920™;

DNA was quantified using PCR standard curves that were established using synthetic targets.

The nucleic acid amplification medium used in these experiments was a LAMP reaction mixture that included a fluorophore (EvaGreen dye) to allow the progress of amplification to be fluorescently monitored. A 25 µL volume of this LAMP reaction mixture contains the following: 3.5 µL of 10 mM dNTPs (New England Biolabs, Ipswich, Mass.), 2.5 µL of 10× Isothermal Amplification Buffer (New England Biolabs), 2 µL of 5M Betaine (Sigma-Aldrich), 1.5 µL of 100 mM Magnesium Sulfate Solution (New England Biolabs), 2 µL of primer mix, 2 µL of 8000 units/mL Bst 2.0 Warmstart DNA Polymerase (New England Biolabs), 1.25 µL of 20× EvaGreen Dye (Biotium, Fremont, Calif.), 2.25 µL of DEPC-treated water (Invitrogen, Carlsbad, Calif.), and 8 µL of the template DNA (New England Biolabs).

Initially, the LAMP reactions were carried out on a benchtop thermocycler (Mastercycler® RealPlex; Eppendorf, Hamburg, Germany) at 65° C. for 40 minutes and terminated by heating at 85° C. for 5 minutes. The 25 µL reaction mix was divided into three equal parts (8 µL) for triplicate repetition. Ten-fold serial dilutions of the extracted DNA were carried out in DEPC-treated water to determine the working range of the LAMP assays.

The endpoint images of the nucleic acid amplification reactions captured by the smartphone-based instruments are in the format of JPG, and they can be exported out of the smartphone to be analyzed with Matlab or analyzed through a custom-built Android App. The Matlab analysis starts with the importing of the image as a 3120×4160×3 matrix. The first two dimensions represent the size of the image, and the last dimension provides a 24-bit RGB (red, green, blue) color space. Each of the RGB intensity components of each pixel is stored as an 8-bit unsigned integer ranging from 0 to 255. Since the fluorescence light emitted from the fluorophore (EvaGreen dye) is green in color and centered at 530 nm in spectrum, only the G channel intensity is used in the following image processing. The spatial location for each of the 10 lanes can be recognized through a boundary detection method. Within each lane, which usually covers a range of 40×700 pixels, the average and standard deviation (STD) of all the pixel intensities are calculated. The average intensity obtained from lane 2, which is the negative control, indicates the background intensity of the fluorescence measurement. For this reason, it is used as the baseline and subtracted while computing the final output intensity of all the other lanes. The Android app processes the images in a similar manner. After the images are captured by the smartphone, the boundary detection algorithm is applied to help find the locations of the ten lanes. The average value of each lane is computed and shown on the screen.

b. Results and Discussion

FIGS. 10A-10D show the results (as fluorescence images of the microfluidic lanes of the amplification module and as bar graphs of the fluorescence intensity in each lane) for the four experiments performed for the detection of each of the four types of pathogens. For the experiment shown in FIG. 10A, the sample loaded into the chip contains $5\times10^7$ copies/mL S. Equi DNAs. As seen in the fluorescence image, lane 3 and 4, where the S. Equi primers are located, become as bright as the positive control (lane 1). To quantitatively analyze the fluorescence image, the average intensities of the ten lanes were determined as described above. A threshold value was selected as half the value of the positive control. As shown in the bar graph of FIG. 10A, the intensities of lane 3 and 4 (which were loaded with primers for S. Equi) are significantly higher than the threshold, whereas the intensities lanes 5 through 10 (which were loaded with primers for other pathogens) are well below the threshold. The variations in the intensities of lanes 5 to 10 can be attributed to differences in background fluorescence intensity and/or variation in illumination intensity from the LEDs.

Figure 10A:
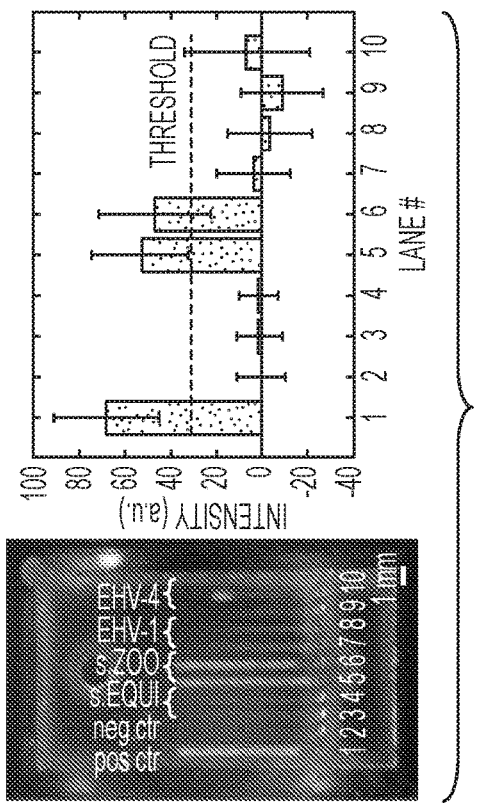
FIGS. 10A-10D show results (as fluorescence images of the microfluidic lanes of the amplification module and as bar graphs of the fluorescence intensity in each lane) obtained using a sample carrier as shown in FIGS. 2A-2B and a detection instrument as shown in FIGS. 5A, 5B, and 6 for samples containing S. Equi DNA (FIG. 10A), S. Zoo DNA (FIG. 10B), EHV-1 DNA (FIG. 10C), and EHV-4 DNA (FIG. 10D), in accordance with an example embodiment.
Figure 10B:
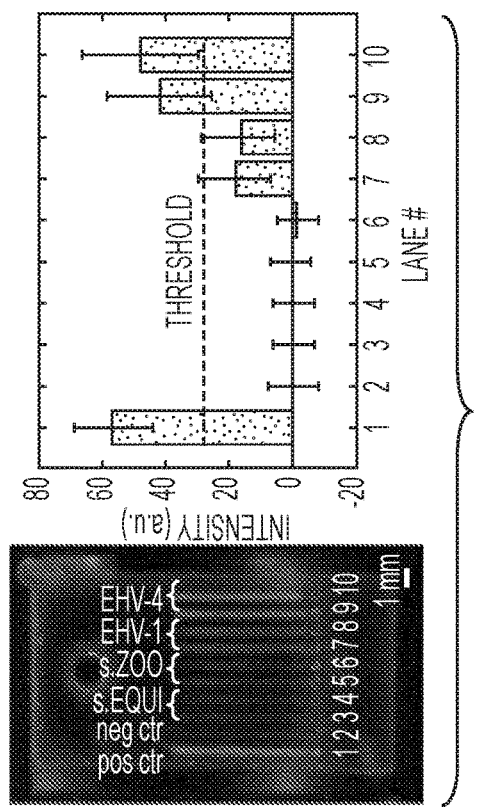
Figure 10C:
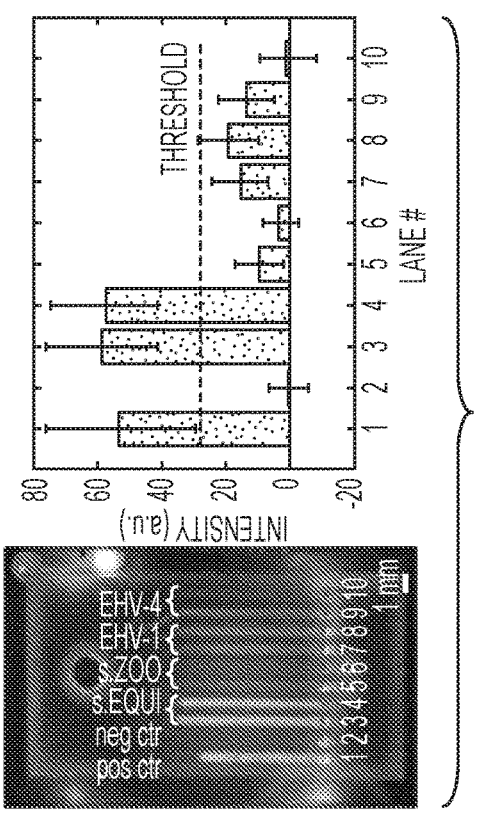
Figure 10D:
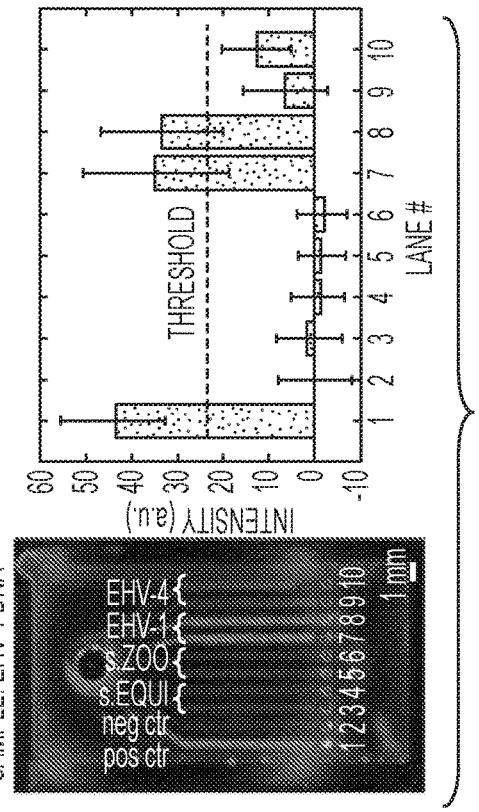

Similar experiments were done with the other three types of pathogens. FIG. 10B shows the results for the S. Zoo DNAs at a concentration of $5\times10^6$ copies/mL. Lanes 5 and 6 stand out clearly in terms of fluorescence intensity, consistent with lanes 5 and 6 having been loaded with primers for S. Zoo. FIGS. 10C and 10D show the results for EHV-1 and EHV-4, respectively. The concentration for the injected EHV-1 and EHV-4 DNAs were $5\times10^6$ copies/mL and $2\times10^6$ copies/mL, respectively. For EHV-1 shown in FIG. 10C, only lanes 7 and 8 are bright, consistent with lanes 7 and 8 having been loaded with primers for EHV-1. For EHV-4 shown in FIG. 10D, only lanes 9 and 10 are bright, consistent with lanes 9 and having been loaded with primers for EHV-4. Thus, as shown in FIGS. 10A-10D, when the lanes are exposed to DNA from a specific pathogen, only the lanes where the specific pathogen's primers are deposited generate fluorescence intensity that is higher than the threshold value. Thus, the fluorescence intensity at the endpoint of nucleic acid amplification in a given lane can be compared to a threshold value (e.g., half of the fluorescence intensity of the positive control after subtracting out the fluorescence intensity of the negative control) to determine qualitatively whether the pathogen corresponding to the given lane is present or undetectable in a sample.

Figure 11:
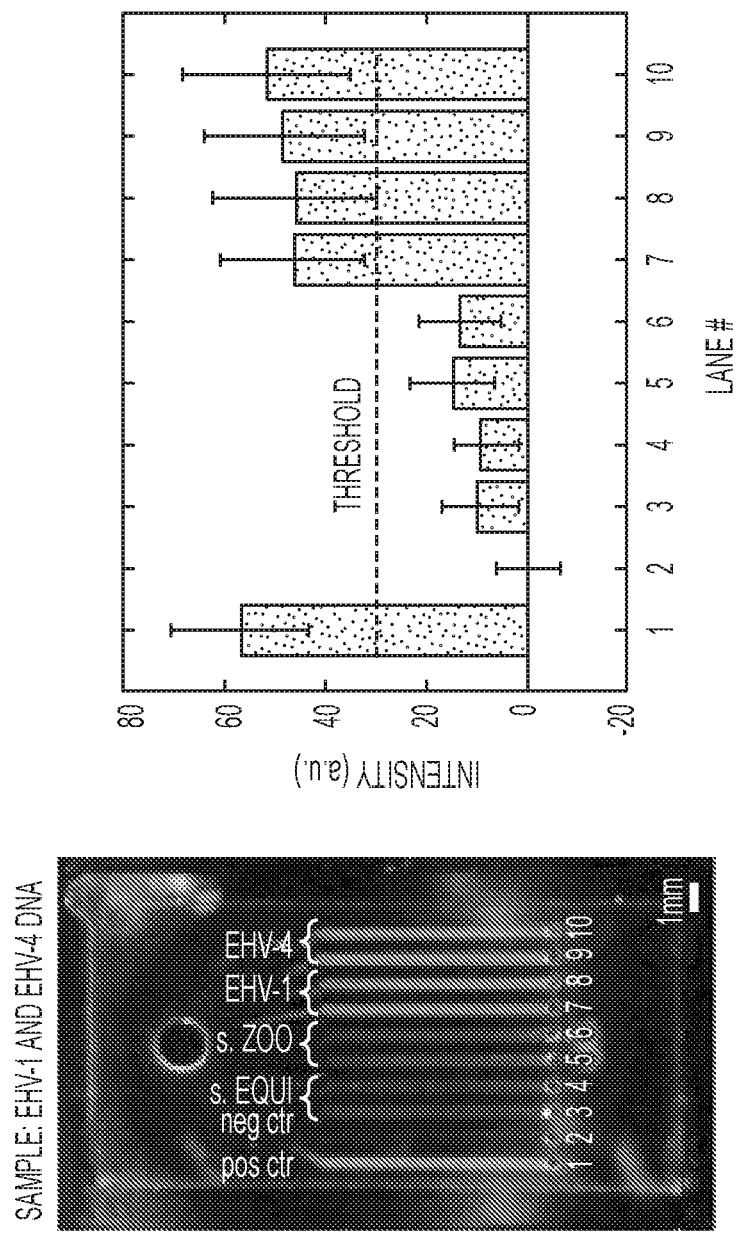
FIG. 11 shows results (as fluorescence images of the microfluidic lanes of the amplification module and as bar graphs of the fluorescence intensity in each lane) obtained using a sample carrier as shown in FIGS. 2A-2B and a detection instrument as shown in FIGS. 5A, 5B, and 6 for a sample containing both EHV-1 DNA and EHV-4 DNA, in accordance with an example embodiment.

This approach can also be used to detect more than one type of pathogen in a single sample, representing co-infection by multiple pathogens. FIG. 11 shows the results (as a fluorescence image of the microfluidic lanes of the amplification module and as a bar graph of the fluorescence intensity in each lane) for a sample containing $4\times10^4$ copies/mL EHV-1 DNAs and $3.2\times10^5$ copies/mL EHV-4 DNAs, with the lanes 1-10 configured as described above. As shown, the fluorescence intensities of lanes 7 and 8 (corresponding to EHV-1) and lanes 9 and 10 (corresponding to EHV-4) are greater than the threshold value, whereas the fluorescence intensities of lanes 2 and 3 (corresponding to S. Equi) and lanes 4 and 5 (corresponding to S. Zoo) are less than the threshold value. Thus, it is anticipated that various combinations of different types of pathogens present in a sample can be detected in this way.

6. Example Application 2: Detection of Zika, Chikungunya, and Dengue

The smartphone-based system shown in FIGS. 5A, 5B, and 6 and described above was validated using a sample carrier shown in FIGS. 3A, 3B, and 3C to detect Zika, Chikungunya, and Dengue.

a. Materials and Methods

Sample preparation modules as shown in FIG. 3B were fabricated in accordance with the following description. Polydimethylsiloxane (PDMS) was synthesized and poured over a SU-8 master mold fabricated using standard cleanroom photolithography techniques. The PDMS was then degassed in a vacuum desiccator and incubated in a 60° C. oven for 2-3 hours to cure. A block of cured PDMS with a thickness of approximately 5 mm was then cut out from the mold and cleaned with Isopropyl Alcohol (IPA) followed by drying with dry nitrogen to remove impurities from the microfluidic channels. Three inlet holes and one outlet hole were drilled into the PDMS using a 0.5 mm needle, for tubing connections. Afterwards, the surfaces of the processed PDMS and a clean glass slide were activated using an oxygen plasma system (Pico; Diener, Ebhausen, Germany). Immediately following this, the PDMS and glass slide were covalently bonded to each other over a hot plate at 120° C. to form the complete sample preparation module. The sample preparation module included three inlet ports for receiving three different fluids: a sample inlet port for receiving whole blood spiked with whole Zika virus particles or viral RNA; an amplification medium inlet for receiving RT-LAMP reagent (nucleic acid amplification medium); and a lysis medium inlet for receiving a cell lysis medium. The flow rates were controlled using syringe pumps, and were fixed at 1 µL/min, 3 µL/min, and 10.62 µL/min for virus/RNA in whole blood, lysis buffer, and RT-LAMP reagents respectively. This setup was kept in the biosafety cabinet, and biosafety level 2 protocols were followed during these experiments.

The spiked blood samples were prepared as follows. Whole Zika virus particles (PRVABC59 and MR-766 strains) were purchased from BEI Resources (Manassas, Va.). The stock vial was aliquoted and stored at −80° C. Appropriate stock volumes were used either for direct experimentation with the viruses or for RNA extraction. For experiments using whole viruses directly, the appropriate stock volume of the virus was taken and diluted to the right concentrations either in whole blood or lysed blood. The whole venous blood samples were drawn from healthy, consenting, Zika-negative adult volunteers with a syringe and later transferred to 4 mL BD Vacutainer K2 EDTA collection tubes. The tubes were stored in a sample rotisserie at room temperature before using them for experiments.

Zika virus RNA was purified from whole Zika virus particles using RNeasy Mini Kit (Qiagen, Hilden, Germany). Genomic RNA from Dengue Virus Type 1, Hawaii, NR-4287, and genomic RNA from Dengue Virus Type 3. Philippines/H87/1956, NR-2771 was obtained through BEI Resources, NIAID, NIH. Quantitative Synthetic Chikungunya virus RNA (ATCC® VR3246SD™) was purchased from American Type Culture Collection (ATCC). The purified RNA was aliquoted and stored at −80 C until used for experiments. The stock viral RNA was diluted in either DPEC water or whole blood depending on the experiments.

The RT-LAMP reagent (nucleic acid amplification medium) included the following to components: 1× final concentration of the isothermal amplification buffer (New England Biolabs), 1.4 mmol/L each of deoxy-ribonucleoside triphosphates (dNTPs), 10 mmol/L of $MgSO_4$. (New England Biolabs), and 0.4 mol/L of Betaine (Sigma-Aldrich). These components were prepared in bulk and stored at a temperature of −20° C. between experiments. In addition, 3 µL of primer mix consisting of 0.2 µM of F3 and B3, 1.6 µM FIP and BIP, and 0.8 µM of LoopF and LoopB, 0.64 U/µL Bst 2.0 WarmStart DNA Polymerase (New England Biolabs), 0.08 U/µL AMV reverse transcriptase (New England Biolabs), and 1× EvaGreen (Biotium), a dsDNA intercalating dye, was included. A 8 µL template of the appropriate concentration and 0.05 µL of DEPC-treated water (invitrogen) was added to make the final reaction volume 25 µL.

The cell lysis medium consisted of 2.5 mmol/L $KHCO_3$, 37.5 mmol/L $NH_4Cl$, and 0.025 mmol/L EDTA. For all experiments involving lysed blood, a 1:4 ratio of blood to lysis medium was used. A manual pipettor was used to gauge and mix blood with lysis medium for all off-chip experiments on a benchtop thermocycler. For microfluidic on-chip RT-LAMP experiments with whole virus particles/viral RNA in blood, lysis medium and blood were mixed using the sample preparation module. The flow rates for the blood and lysis medium into the sample preparation module was set to 1:4, using two syringe pumps.

Amplification modules as shown in FIG. 3C were fabricated as follows. A 4-inch <100> silicon wafer (University Wafer, South Boston, Mass.) with one side polished was thoroughly cleaned and used as the substrate in the photolithography process. Positive photoresist SPR 220 (MicroChem, Newton, Mass.) was spin-coated on the polished side of the wafer to form a 4.5 µm covering layer, followed by a soft-bake at 60° C. for 2 min and 110° C. for 1 min. The photoresist was then exposed with an i-line (365 nm) mask aligner (EVG 620) with an expose dose of 180 $J/cm^2$. The exposed regions of the photoresist with the outline of the microfluidic pattern were subsequently removed by immersing the wafer in AZ developer diluted 1:4 with deionized (DI) water for about 4 minutes. The photoresist in the unexposed regions was solidified though a hard-bake at 110° C. for 1 min. For anisotropic etching of the silicon substrate, a Bosch process with alternating steps of $SF_6/O_2$ etching and $C_4F_8$ passivation was used to create 200 µm deep trenches in an inductively coupled plasma reactive ion etcher (ICP-RIE). After the etching, the remaining photoresist was stripped with acetone and $O_2$ plasma cleaning, leaving the bare silicon exposed. Because bare silicon has been reported to have inhibitory effects on nucleic acid amplification due to absorption of polymerase, the silicon wafer was thermally oxidized in a furnace (1150° C.) for 2 hours to grow a 200 nm film of $SiO_2$. The wafer was then diced into individual amplification module chips.

Before the primers were deposited, each amplification module chip was cleaned as follows. First, the chip was cleaned in a Piranha solution containing 1:3 of 30% hydrogen peroxide and 98% sulfuric acid for 10 minutes followed by extensive rinsing with DI water to remove any acidic residues. Then, the chip was dried using nitrogen gas and immersed in Sigmacote (Sigma-Aldrich) in a sterile petri dish for approximately 5 minutes to make the surface of the chip and its channels hydrophobic. This is done to prevent any non-specific adsorption of biomolecules on the chip surface during the RT-LAMP reactions. The chip was then rinsed with IPA before being blow-dried with nitrogen gas. Chips were placed in sterile glass petri dishes until use.

Primers were printed on the positive and non-template negative flow channels in the amplification modules followed by a short incubation period at room temperature to dry the primers. Briefly, 1× concentration of the primer was diluted in 1:3 ratio in DEPC-treated water. Then two drops of 0.24 µL of primers were pipetted using a 0.5-10 µL pipette along the center of the positive reaction lanes equidistant from each other. Afterwards, DSA membranes (Adhesives Research), each with 11 laser-cut holes, attached to three small PDMS blocks with holes drilled by a 0.5 mm needle was aligned and attached to the amplification modules. PDMS blocks were aligned with three inlet ports on the chip: a central inlet port for sample injection and two peripheral inlet ports for injection of non-template negative controls. The specific primers that were used in the experiments are identified below in Table 2.

TABLE 2

| | |
|---|---|
| Zika (PRVABC59 strain) RT-LAMP primers | F3: GAC CCC ATC AAC GTG GTG |
| | B3: CCA CAC TCT TTC CTG AGA CC |
| | FIP: TCA GGC CAA CAG CTG TGA GTA CGA CTG CTG TTG CTC ACA AGG |
| | BIP: CGC ATT GGC TGG AGG GTT CGT GAC AAT TAG CAG ACC GAC C |
| | Loop F: CAG CTC CGC TTC CCA CT |
| | Loop B: AGG CAG ATA TAG AGA TGG CTG G |
| Zika (MR-766 strain) RT-LAMP primers | F3: TTC GTG GAG GGC ATG TCA |
| | B3: GAC TGT CCG AAG CCA TGT C |
| | FIP: CCT GTG CCA TCA CGG TAA CGC GGT GGG ACC TGG GTT |

TABLE 2-continued

|   |   |
|---|---|
| | GAT<br>BIP: TAG ACT TGG TCA CGA CGA CGG TCG ATA TCG ATG CCT CGT AGC<br>Loop F: AGC CTC CAT GTT CCA AGA CAA<br>Loop B: AAC ATG GCC GAG GTA AGA TCC |
| Dengue-1<br>RT-LAMP primers | F3: TGT GTT CCT CCT TCT CAT AAT G<br>B3: CAG ACT CAA TCC AAT CGT AAG A<br>FIP: CAT CCT GTC TGA AGC ATT GGC TGG ACA ATT GAC ATG GAA TGA TC<br>BIP: CCT AGC TCT GAT GGC CAC TTT CTT CTC TAG ATG TTA GTC TGC G<br>Loop F: CCA ACC ATG ATG CAT AAC CTG<br>Loop B: ATG AGA CCA ATG TTC GCT GT |
| Dengue-3<br>RT-LAMP primers | F3: CCC GTC CAA GGA CGT TAA<br>B3: CTG CTG CGT TGT GTC ATG<br>FIP: CG ACG GAG CTA CAG GCA GAA GAA GTC AGG CCC AAA<br>BIP: GGG ACG TAA AGC CTG GGA GCC TCT AAC CAC TAG TCT GCT A<br>Loop F: GTT TGC TCA AAC CGT GGC<br>Loop B: AAC CGT GGA AGC TGT ACG |
| Chikungunya<br>RT-LAMP primers | F3: ACG CAA TTG AGC GAA GCA C<br>B3: CTG AAG ACA TTG GCC CCA C<br>FIP: CGG ATG CGG TAT GAG CCC TGT ATG GAG AAG TCC GAA TCA TGC<br>BIP: TCC CCC TCC TTT ACC AAG GAA ATT TGG CGT CCT TAA CTG TGA C<br>Loop F: GCT GAT GCA AAT TCT GT<br>Loop B: CCT ATG CAA ACG GCG AC |
| Zika Envelope<br>RT-PCR primers | Forward: CCG CTG CCC AAC ACA AG<br>Reverse: CCA CTA ACG TTC TTT TGC AGA CAT |

For experiments with viral nucleic acids in water, the template and the RT-LAMP reagents were mixed and then injected into the amplification module using a syringe pump. Once the sample was loaded into the amplification module, the outer layer of the DSA which contained the PDMS blocks was peeled off, and the amplification module was sealed with a second DSA layer to prevent evaporation during RT-LAMP incubation. The chip was placed on a card to form a sample carrier, and the sample carrier was inserted into the detection instrument for real-time monitoring.

For experiments involving blood, the sample preparation module and the amplification module were mounted on a card to form a sample carrier as shown in FIG. 3A. A tube connected the outlet of the sample preparation module sample inlet of the amplification module. The amplification module was visually observed for filling, and the connecting tube was manually disconnected once filling was complete. The amplification module was sealed in the same procedure as described above. The sample carrier was inserted into the detection instrument for real-time monitoring.

The detection instrument used in these experiments was as shown in FIGS. 5A, 5B, and 6, except that the light sources were powered by an Arduino Gemma microcontroller system, which included a programmable circuit board and control software. The microcontroller system was powered by a lithium-ion battery (3.7 V) and provides 3.3V output by a built-in voltage regulator that powers all eight LEDs consistently. The preprogrammed Arduino board regulates the duty cycle and operation frequency of the LED On-Off switching during a measurement. For experiments with viral RNA in water, the LED "on" time was 6.1 seconds, and the "off" time was 53.9 seconds. For experiments with whole virus particles or RNA in whole blood, the LED "on" time was set to 10 seconds, and the "off" time was set to be 50 seconds.

Due to safety considerations, the imaging function of the smartphone was remote controlled. IP Webcam is an Android application that allows the user to transmit live images over a wireless network, which can be subsequently observed in real time in a web browser. IP Webcam was downloaded from the Google Play Store and installed on the smartphone. The remote browser control allowed regulation of the smartphone camera's zoom, exposure, gain, stream quality and imaging/video recording capabilities. Two different sets of parameters were used for imaging of viral nucleic acids in water and whole virus particles or RNA in whole blood. The following parameters were used in IP Webcam for imaging of RT-LAMP reactions using viral nucleic acids: 1.42× zoom, 99% stream quality, and night vision function with a gain of 10× and an exposure of 3. For imaging of RT-LAMP reactions using whole blood spiked with whole virus particles or viral nucleic acids, the following parameters were used: 1.42× zoom, 99% stream quality, and night vision function with a gain of 15× and an exposure of 10.

Images recorded with IP Webcam in the smartphone were saved in TIFF format from which fluorescence intensity was analyzed in an automated fashion using a MATLAB script. Grayscale images were first imported as an array of 8-bit unsigned integers (range 0-255), which represented each pixel in the image. Then, the average fluorescence intensity from only the channel portions of the amplification module were extracted using a polygonal virtual mask. Such time-lapsed fluorescence values for each channel were obtained from the time-lapsed images of the amplification module and a fluorescence vs time curve was plotted. The baseline (initial) fluorescence value was subtracted for each curve to account for the differences in starting fluorescence values per channel.

All on-chip and off-data RT-LAMP and RT-PCR data was analyzed and plotted using a MATLAB script. For all the off-chip and on-chip experiments, the threshold time was taken as the time taken for an amplification curve to reach 20% of its maximum intensity. For on-chip reactions (i.e., reactions occurring in the amplification module), the fluorescent intensity on-chip was extracted from each channel and was plotted against time to generate the raw fluorescence curves. Each raw amplification curve was fitted to a sigmoidal curve using four-point parameter modeling. The following equation was used for the analysis:

$$f = y_0 + \frac{a}{1 + e^{-\left(\frac{x-x_0}{b}\right)}}$$

In this equation, f=fluorescence intensity, $y_0$=background fluorescence at time=0 minutes, a=difference between the initial and final fluorescent intensity, x=time point of analysis, $x_0$=inflection point of the curve, and b=slope of the curve. The threshold time was obtained at the point where the fluorescent intensity=$y_0$+0.2*a. The positive and negative wells were differentiated on the basis of the $R^2$ value of the sigmoidal fit and the parameters a and $x_0$. The threshold time was taken as the point of inflection. Negative wells had a combination of low $R^2$ value, low a value, or a very high threshold time ($x_0$>50 minutes).

b. Results and Discussion

Figure 12F:
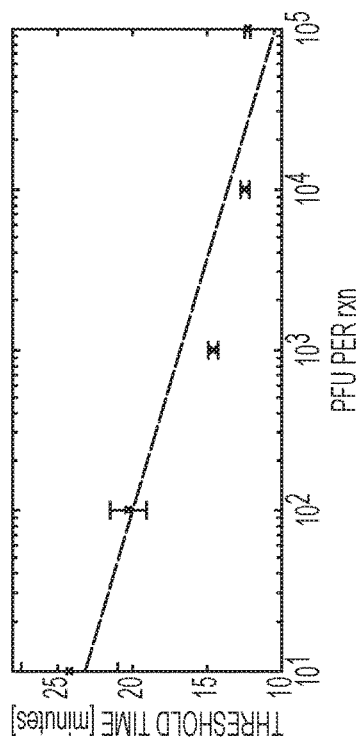

The Zika PRVABC59 strain was isolated from the blood of a human in Puerto Rico in December 2015, and the NS1 gene in Zika has previously been used for specifically detecting Zika using RT-PCR assay. FIGS. 12A-12F show the results of an off-chip characterization of the RT-LAMP assay in a benchtop thermocycler apparatus. FIG. 12A shows curves that represent the baseline-subtracted change in fluorescent intensity over time for different concentrations of Zika RNA, and FIG. 12B is a plot of the corresponding threshold time against the PFU equivalent of purified RNA per reaction. A good linear fit is observed for the standard curve ($R^2$=0.9755), with a lower limit of detection of 10 PFU equivalent of purified RNA per reaction (reaction volume=25 μL) corresponding to 1250 PFU/mL purified RNA in starting concentration.

The Zika RT-LAMP reaction was also compared with a previously published CDC RT-PCR assay for Zika. S. Lanciotti, O. L. Kosoy, J. J. Laven, J. O. Velez, A. J. Lambert, A. J. Johnson, S. M. Stanfield, and M. R. Duffy, "Genetic and Serologic Properties of Zika Virus Associated with an Epidemic, Yap State, Micronesia, 2007," 14 (2008) 1232-1239. The comparison was carried out using RT-PCR experiments with the same Zika RNA concentrations as used for RT-LAMP using the CDC RT-PCR primers and obtained the amplification and standard curves. FIG. 12C shows curves that represent the baseline-subtracted change in fluorescent intensity over time for different concentrations, and FIG. 12D is the corresponding standard curve for the RT-PCR assay. The lower limit of detection for the RT-PCR assay was found to be 1 PFU equivalent of purified RNA per reaction (20 μL) corresponding to 370 PFU/mL purified RNA in starting concentration.

Figure 12E:
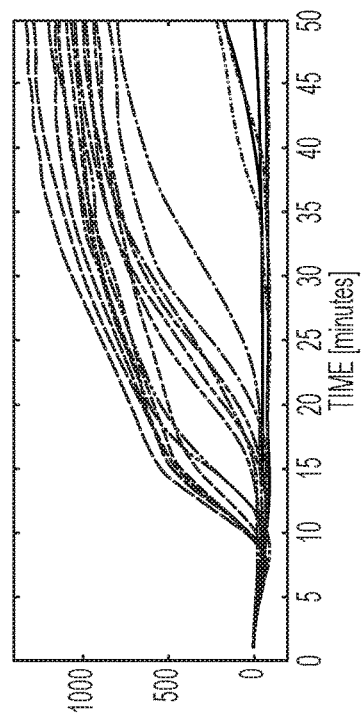

To characterize the feasibility of the RT-LAMP reaction from minimally processed samples, different concentrations of whole Zika viruses were spiked in lysed whole blood and the reactions were performed in the thermocycler. FIG. 12E shows curves that represent the baseline-subtracted change in fluorescent intensity over time for different concentrations of viruses, and FIG. 12F is a plot of the corresponding threshold times for the different concentrations. Similar to the RT-LAMP reaction with purified RNA, Zika spiked in lysed whole blood showed a good linear fit for the standard curve ($R^2$=0.9047) and a lower limit of detection of 10 PFU per reaction in 25 μL tube based reactions. This corresponded to a starting Zika sample concentration of 6250 PFU/mL in blood. These results show that the RT-LAMP reaction is robust to the debris present in lysed whole blood.

Figure 13B:
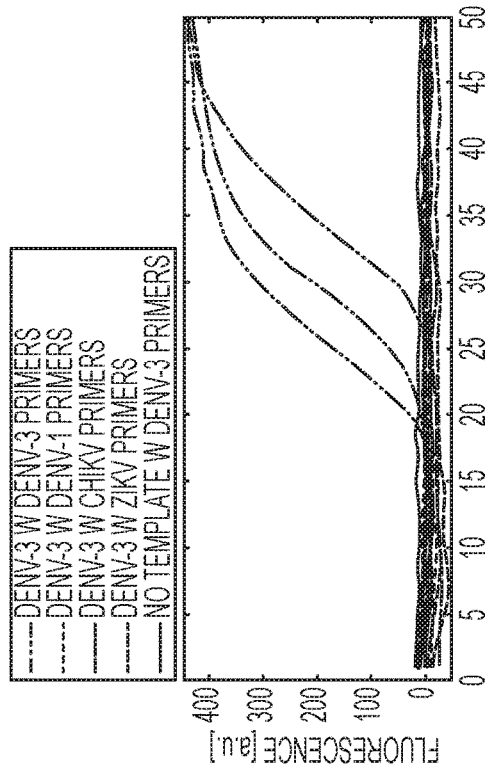
FIGS. 13A-13D show the baseline-subtracted raw amplification curves representing changes in fluorescence over time for the RT-LAMP reactions from lysed whole blood spiked with DENV-1 RNA (FIG. 13A), DENV-3 RNA (FIG. 13B), CHIKV RNA (FIG. 13C), and ZIKV RNA (FIG. 13D), in accordance with an example embodiment.
Figure 13A:
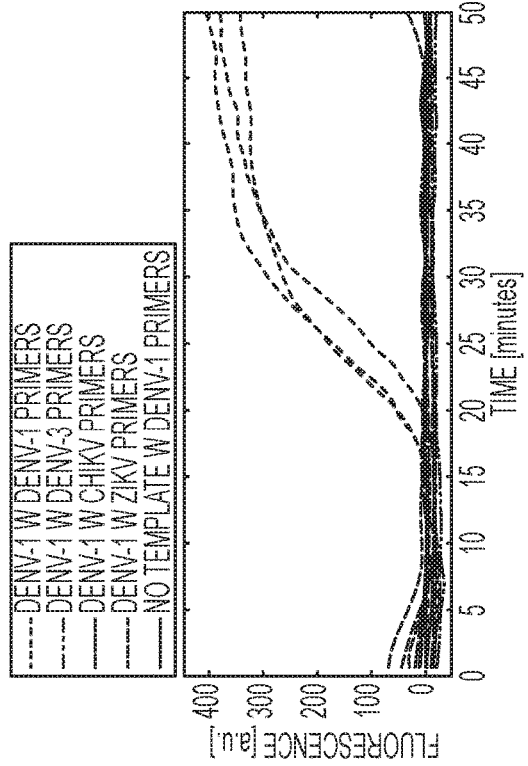
Figure 13D:
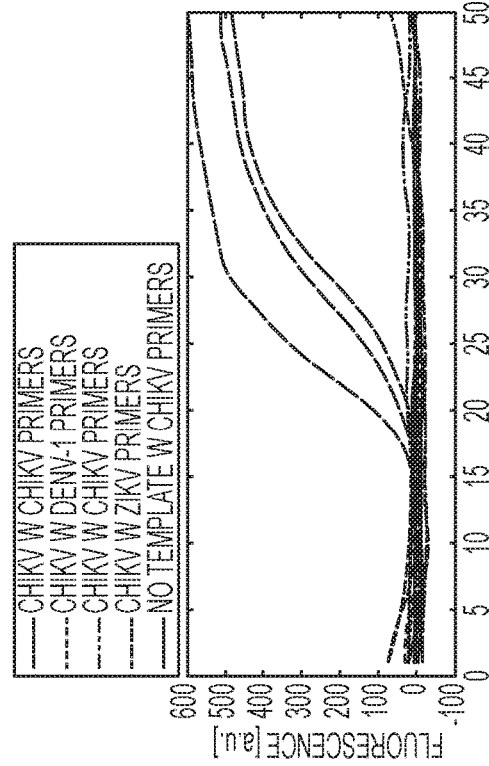
Figure 13C:

The ability to perform multiplexed pathogen detection among Zika virus (ZIKV) and the closely related viruses, Dengue virus (DENV; strains 1 and 3) and Chikungunya virus (CHIKV) was validated in a tube-based thermocycler reaction using the primers identified in Table 2. FIGS. 13A-13D show the baseline-subtracted raw amplification curves representing changes in fluorescence over time for the RT-LAMP reactions from lysed whole blood spiked with DENV-1 RNA (FIG. 13A), DENV-3 RNA (FIG. 13B), CHIKV RNA (FIG. 13C), and ZIKV RNA (FIG. 13D). Each of the samples was challenged with all of the primer sets (ZIKV primers, CHIKV primers, DENV-1 primers, and DENV-3 primers). These results demonstrate that the viral RNA samples are amplified only in the lanes that include the corresponding primers.

The sample preparation module was validated as follows. 10 μL of whole blood sample spiked with 625 PFU/μL Zika virus was metered and injected into the sample preparation module concurrently with lysis buffer and RT-LAMP reagents through the corresponding inlets. The output from the sample preparation module was collected on four separate instances, and RT-LAMP experiments on each instance were performed on the thermocycler. As a control, four replicates of the same Zika virus spiked whole blood sample was mixed with lysis buffer and RT-LAMP reagents manually using a pipette and analyzed in a thermocycler. FIG. 14A shows baseline-subtracted raw amplification curves showing the changes in fluorescence over time for the four outputs of the sample preparation module (on-chip mixing) and for the four replicates mixed manually (off-chip mixing). FIG. 14B shows bar graphs comparing the threshold times determined from the curves in FIG. 14A for the on-chip mixing and the off-chip mixing. The threshold times for these two processing techniques were found to very similar, with the deviation in the on-chip processing threshold time being 3.6% from the off-chip processing threshold time.

After the characterization of the RT-LAMP reactions in the thermocycler ("off-chip"), these reactions were characterized in the amplification module ("on-chip") using the smartphone-based detection instrument described above. RT-LAMP reactions with purified Zika virus RNA in water and Zika virus spiked in whole blood were performed in the amplification module with ten-fold serial dilutions, and the working range and limit of detection of the assays were determined. The PTC heater in the detection instrument maintained a temperature between 64-66° C., which was appropriate for the reactions to take place. Real-time images were captured by smartphone and threshold time analysis was performed using a MATLAB script. For both sets of experiments, 3 alternating channels (in the primary hexagon shape) on the microchip, and 2 separate non-template negative control channels on the chip periphery were printed with Zika primers. The remaining 3 channels are left unprinted to serve as on-chip no-primer controls which are simultaneously performed in each experimental run. Thus the chip in total has 3 positive reaction channels, 3 negative no-primer control channels, and 2 negative no-template control channels as shown in the chip layout. Together they ensure that the amplification results obtained are from Zika-specific reactions only and not from spurious, non-specific amplification.

For the on-chip RT-LAMP characterization with purified Zika RNA, template (purified Zika RNA in water) and the RT-LAMP reagents without primers was mixed manually using a pipette, and 7 μL of the final reaction mix was injected into the amplification module using a syringe pump. The amplification module was sealed to prevent evaporation and contamination. A sample carrier consisting of the sealed amplification chip mounted on a card was inserted into the detection instrument. FIG. 15A shows raw fluorescence images of the amplification module at time=0, 14, 28, and 42 minutes, which indicate amplification of only the positive channels for RT-LAMP reaction with purified Zika RNA. The images shown are for RT-LAMP reaction from 10 PFU equivalent of purified RNA per microliter of Zika virus. FIG. 15B shows the raw amplification curves for the on-chip amplification of purified Zika RNA, FIG. 15C shows the amplification curves after sigmoidal fitting, and FIG. 15D shows the threshold-time standard curves for these reactions. This data shows a lower limit of detection of purified Zika RNA equivalent to 10 PFU per reaction (1 channel=1 reaction=1 μL volume), corresponding to $3.125 \times 10^4$ PFU/mL in starting concentration. A good linear fit was observed in the standard curve ($R^2$=0.99) with distinct threshold times per ten-fold change in template concentration.

A sample carrier with the sample preparation module connected to the amplification module was used to characterize the RT-LAMP reactions with Zika virus in whole blood. The Zika virus infected blood sample was first processed in the sample preparation module (using the lysing medium) and then allowed to flow into the amplification module. Upon filling, the amplification module was sealed, and the sample carrier was inserted into the detection instrument. FIG. 15E shows the raw amplification curves carried out on-chip with whole Zika viruses in blood, FIG. 15F shows the amplification curves after sigmoidal fitting, and FIG. 15G shows the threshold-time standard curves for these reactions. A good linear fit was observed in the standard curve ($R^2$=0.9913) with Zika virus detection down to copies per μL of final reaction (1 channel=1 reaction=1 μL volume), corresponding to $1.56 \times 10^5$ PFU/mL starting virus concentration. With clinically significant detection limits from infected blood samples, these results demonstrate that the on-chip assay can successfully monitor viral loads via RT-LAMP reactions with hands-free sample processing, a portable detection instrument, and smartphone-based imaging that can be easily translated for use at the point-of-care.

Figure 16A:
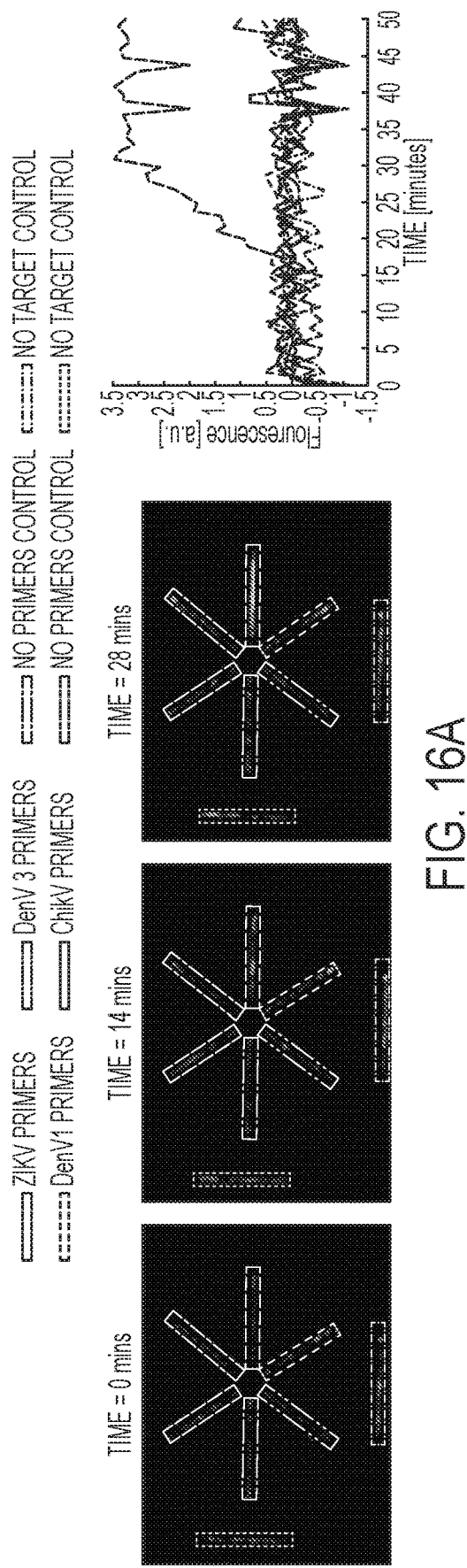
Figure 16B:
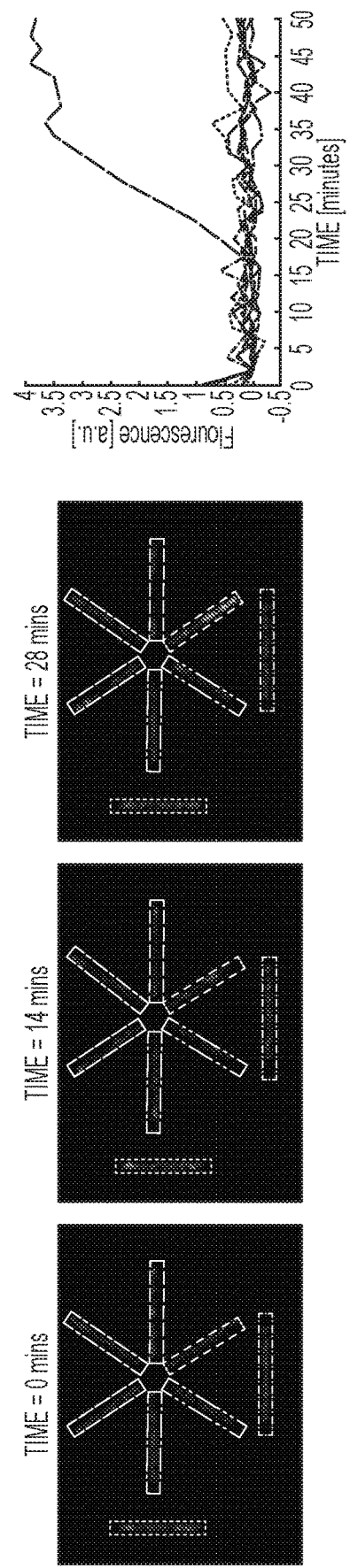

The platform was also validated for analyzing samples containing different pathogens. Primers for Zika, Dengue-1, Dengue-3, and Chikungunya primers were printed in different channels of the amplification module. Samples with either $1.56 \times 10^4$ PFU/μL of whole Zika virus in whole blood or $1.56 \times 10^4$ copies/μL of purified RNA of either Dengue-1 (DENV-1), Dengue-3 (DENV-3), or Chikungunya (CHIKV) in whole blood were assayed in a sample carrier with a sample preparation module and amplification module using the smartphone-based detection instrument described above. FIGS. 16A-16D show raw fluorescence images of the amplification module, together with raw amplification curves of the RT-LAMP reaction for the samples containing whole Zika virus (FIG. 16A), DENV-1 viral RNA (FIG. 16B), DENV-3 viral RNA (FIG. 16C), and CHIKV viral RNA (FIG. 16D). In each of the case, only the lanes printed with primers specific for a particular pathogen's RNA amplify a sample containing that particular pathogen's RNA (as indicated by increasing fluorescence over time), whereas the remaining lanes remain at baseline fluorescence during the entire reaction. These reactions demonstrate the capability of the platform to specifically diagnose and provide clinically actionable information for different pathogens at the point-of-care from infected whole blood samples.

7. Example Application 3: Spatially Resolved LAMP

Figure 17:
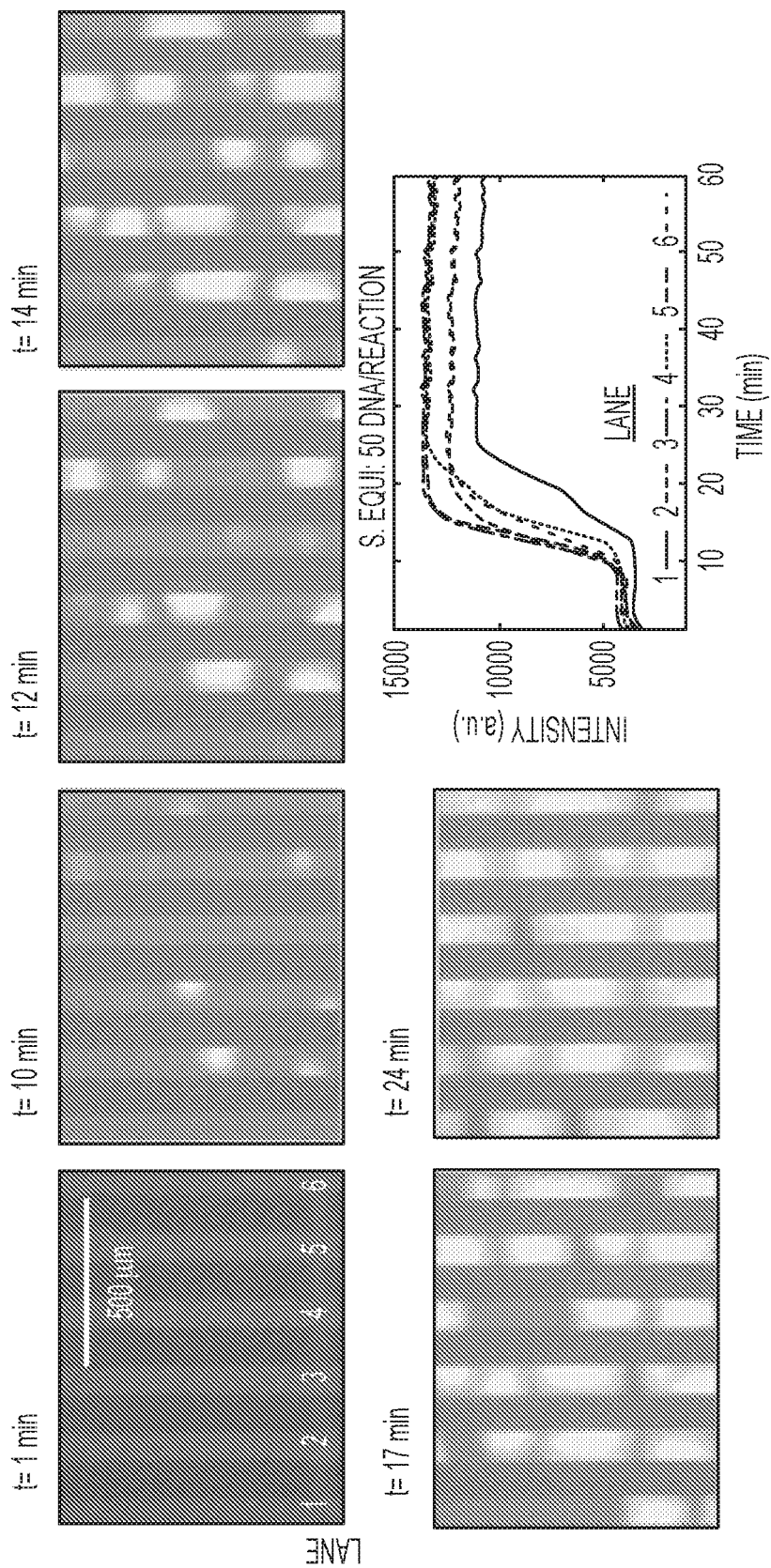
FIG. 17 shows a sequence of fluorescence images at t=1 minute, I=10 minutes, t=12 minutes, t=14 minutes, t=17 minutes, and t=24 minutes, for 6 microfluidic lanes, with each lane containing S. Equi primers and about 50 copies of S. Equi target DNA, and corresponding curves of the fluorescent intensity over time for the lanes, in accordance with an example embodiment.

The image processing in Example Application 1 and Example Application 2 utilized the average fluorescence intensity from an entire microfluidic lane to represent the output of each LAMP assay. However, unlike standard LAMP or PCR processes performed in vials, the images of the microfluidic chambers in the amplification module that are captured by the camera during the amplification process allow the initiation and kinetics of the process to observed with great detail. At high virus concentrations (>500 PFU/reaction) a threshold of fluorescence output typically begins after t=10-20 minutes, but once it begins, is very rapidly and uniformly distributed throughout the lane. In such cases, the threshold time can be used to estimate the virus concentration, as in Example Application 2. However, for concentrations of 1-50 PFU/reaction, initiation of fluorescence signal is typically observed from several independent loci, from which the high-fluorescence regions expand due to diffusion and exponentially increasing concentration of fluorescent product as the LAMP reaction proceeds. In such cases, the threshold time of the entire lane is not as useful for estimating the virus concentration because the lane's brightness is sporadic and nonuniform. For example, FIG. 17 shows a sequence of fluorescence images at t=1 minute, t=10 minutes, t=12 minutes, t=14 minutes, t=17 minutes, and t=24 minutes, for 6 microfluidic lanes, with each lane containing S. Equi primers and about 50 copies of S. Equi target DNA. Loci of LAMP initiation are visible at t=10 minutes, and the loci expand and begin to overlap (t=17 minutes) as the amplification proceeds. Thus, as shown in the sequence of images in FIG. 17, analysis of the fluorescence images during the initial phase—during which individual target nucleic acid molecules serve as the "kernel" for an amplification locus that becomes visible before subsequently expanding to fill the microfluidic channel volume (and eventually overlap with other amplification loci)—provides an opportunity to quantify the target molecules at very low concentrations, independently from the threshold time that may be used to measure an entire lane.

This approach of spatially resolved LAMP (S-LAMP) can use an image processing algorithm that is able to: (1) establish the regions of interest (ROI) within the image; (2) recognize the initiation of positive LAMP reactions based on the positions of amplification loci, and counting the loci; (3) in the presence of previously-identified loci, recognize the formation of new loci in subsequent images; (4) track each loci as it expands its footprint and quantify metrics that can include loci area, loci "front" velocity, total area percentage occupied by loci, and total area percentage still free of loci; and (5) establish a threshold at which loci can no longer be digitally quantified, and transition to conventional "average intensity" method and calculation of amplification threshold time.

To detect the image regions representing the microfluidic compartments, it is possible to use the contrast of the colors of the fluid in the compartments and of the printed material surrounding the compartments. For example, a color edge detection can be applied to find the pixels on the boundary of the compartments, and an efficient Hough transform algorithm can then be used to link these detected edge pixels (eliminating noisy ones) into lines and curves defining the compartment boundaries and hence the compartment regions. Each detected microfluidic compartment region can be associated with a fluid type based on a predetermined configuration of the sample carrier. The detection and identification of the microfluidic compartment regions could be performed on only the first captured image after the sample carrier is inserted into the detection instrument. The pixels identified as being in the microfluidic compartment regions can be established as the ROIs used in subsequent image analysis.

Accurate detection of the initiation points, both in space and time in the captured image sequences, of positive LAMP reactions allows the number of present pathogens in a microfluidic compartment to be enumerated. Let $f(x,y,t)$ be the measured intensity value of the captured S-LAMP image pixel at the spatial location $(x, y)$ and time $t$. The behavior of the signal $f(x,y,t)$ after each amplification initiation can be modeled with a controlled setup. Qualitatively, from the obtained S-LAMP image sequences (e.g., as shown in FIG. 17) it is observed that after an amplification initiation at a spatial location $(x, y)$ and time $t_1$ in the subsequent image $f(x,y,t)$ with $t>t_1$, this single spatial-temporal LAMP loci $(x, y, t_1)$ expands its reaction footprint spatially and reaches a saturated LAMP intensity value within its footprint.

With this observation, the temporal difference S-LAMP signal can be expressed as:

$$\Delta f(x,y,t)=f(x,y,t)-f(x,y,t-1)$$

which is the difference of the current S-LAMP image with the previous S-LAMP image. In the temporal difference S-LAMP image $\Delta f(x,y,t)$ the only significant pixels are either the footprint front of an already initiated reaction locus or a new initiation point. Thus the following algorithm can be used for detection and enumeration of the loci of positive LAMP reaction.

For each new S-LAMP image $f(x,y,t)$ at time $t$:
1) Compute the temporal difference image $\Delta f(x,y,t)$ with the previous S-LAMP image;
2) Detect pixels $(x, y)$ with value $\Delta f(x,y,t)$ above a certain threshold into a binary image;
3) From the detected footprint front regions in the previous image, estimate the fronts in the current image;
4) Mask the estimated front regions out from the binary image;
5) Detect significant pixels in the remaining binary image and, if found, add a new initiation locus $(x_n, y_n, t_n)$; and
6) Update the reaction front regions in the current frame.

Figure 18:
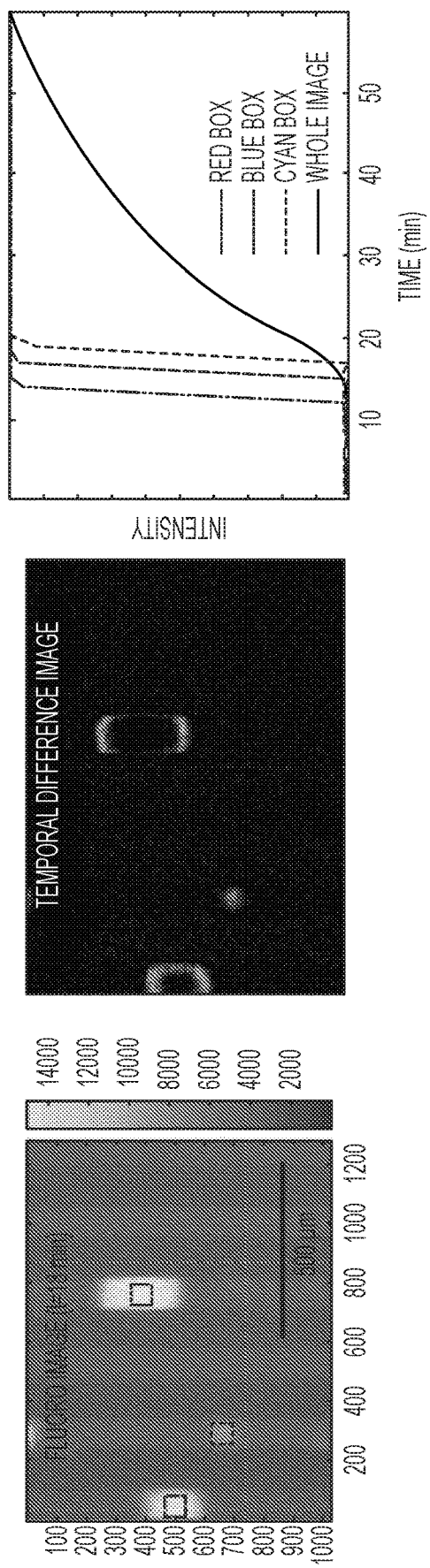
FIG. 18 shows an S-LAMP image with bounding boxes around detected amplification initiation points, a temporal difference S-LAMP image, and curves showing the mean intensity of pixels within the bounding boxes around detected amplification initiation points in comparison with the mean intensity of the whole image as a function of time.

FIG. 18 illustrates the detection and enumeration of target S-LAMP reaction loci. Shown on the left in FIG. 18 is an S-LAMP image with color bounding boxes around detected amplification initiation points. Shown in the middle in FIG. 18 is a temporal difference S-LAMP image clearly showing the footprint fronts of already initiated LAMP loci and a new initiation point. Shown on the right in FIG. 18 are the mean intensity of pixels within the bounding boxes around detected amplification initiation points in comparison with the mean intensity of the whole image as a function of time.

8. Conclusion

Example embodiments have been described herein and shown in the drawings, but not all embodiments of the invention are shown. The invention may be embodied in many different forms and should not be construed as limited to the embodiments set forth herein. Likewise, many modifications and other embodiments of the device, system and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system comprising:
   a sample carrier, wherein the sample carrier comprises an amplification module, wherein the amplification module comprises an amplification-module inlet for receiving a sample and a nucleic acid amplification medium and a plurality of microfluidic chambers fluidly coupled to the amplification-module inlet such that a respective portion of the sample mixed with the nucleic acid amplification medium flows from the amplification-module inlet into each of the microfluidic chambers;
   a housing, wherein the housing has an interior space and a slot through which the interior space is accessible, wherein the slot is configured to receive the sample carrier such that the microfluidic chambers are disposed at a working position within the interior space;
   a plurality of light sources coupled to the housing, wherein each of the light sources is configured to illuminate the microfluidic chambers disposed at the working position with excitation light, wherein a fluorophore in the nucleic acid amplification medium is configured to emit fluorescence light indicative of nucleic acid amplification in response to the excitation light;
   a camera coupled to the housing, wherein the camera is configured to capture images of the microfluidic chambers disposed at the working position; and
   a macro lens disposed in an optical path between the camera and the microfluidic chambers disposed at the working position, wherein the light sources of the plurality of light sources are symmetrically arranged around the macro lens.

2. The system of claim 1, wherein one or more of the microfluidic chambers have disposed therein primers configured to initiate amplification of one or more target nucleic acid sequences.

3. The system of claim 2, wherein the fluorophore comprises an intercalating dye, wherein the excitation light causes the intercalating dye to emit fluorescence light when the intercalating dye is incorporated into amplified nucleic acids.

4. The system of claim 2, wherein the plurality of microfluidic chambers comprises a first microfluidic chamber that has disposed therein a first set of primers configured to initiate amplification of a first target nucleic acid sequence and a second microfluidic chamber that has disposed therein a second set of primers configured to initiate amplification of a second target nucleic acid sequence.

5. The system of claim 2, wherein the nucleic acid amplification medium is configured to amplify nucleic acids at a predetermined temperature by a loop-mediated isothermal amplification (LAMP) process.

6. The system of claim 5, further comprising a heating device coupled to the housing, wherein the heating device is configured to maintain the predetermined temperature within the microfluidic chambers disposed at the working position.

7. The system of claim 6, wherein the heating device comprises a positive temperature coefficient (PTC) heater.

8. The system of claim 1, further comprising a longpass filter disposed in the optical path between the camera and the microfluidic chambers disposed at the working position, wherein the longpass filter passes wavelengths corresponding to the fluorescence light and blocks wavelengths corresponding to the excitation light.

9. The system of claim 1, wherein each of the light sources emits a respective beam of excitation light, and wherein the beams of excitation light from the light sources overlap at the microfluidic chambers disposed at the working position to provide a substantially uniform intensity distribution of the excitation light illuminating the plurality of microfluidic chambers.

10. The system of claim 9, wherein the substantially uniform intensity distribution has an intensity variation that is less than 2% over the plurality of microfluidic chambers.

11. The system of claim 1, wherein each light source of the plurality of light sources comprises a light emitting diode (LED) and a shortpass filter, wherein the shortpass filter passes wavelengths corresponding the excitation light and blocks wavelengths corresponding to the fluorescence light.

12. The system of claim 1, wherein the camera is in a mobile computing device, wherein the mobile computing device is removably mounted to the housing.

13. The system of claim 1, wherein the sample carrier comprises the amplification module mounted on a card.

14. The system of claim 13, wherein the amplification module comprises a substrate and a transparent cover coupled to the substrate, wherein the amplification-module inlet and the microfluidic chambers are defined by channels formed in the substrate and covered by the transparent cover.

15. The system of claim 14, wherein the substrate comprises silicon.

16. The system of claim 13, wherein the sample carrier further comprises a sample preparation module mounted on the card, wherein the sample preparation module comprises a sample-preparation outlet, wherein the sample-preparation outlet is fluidly coupled to the amplification-module inlet.

17. The system of claim 16, wherein the sample preparation module further comprises a blood sample inlet, a lysis medium inlet, and a microfluidic channel fluidly coupled to the blood sample inlet, the lysis medium inlet, and the sample-preparation outlet, wherein the blood sample inlet is configured to receive a blood sample, wherein the lysis medium inlet is configured to receive a lysis medium that lyses cells contained in the blood sample as the blood sample flows through the microfluidic channel toward the sample-preparation outlet.

18. The system of claim 17, wherein the sample preparation module further comprises an amplification medium inlet fluidly coupled to the microfluidic channel, wherein the amplification medium inlet is configured to receive the nucleic acid amplification medium such that the nucleic acid amplification medium mixes with the blood sample as the blood sample flows through the microfluidic channel toward the sample-preparation outlet.

19. The system of claim 18, wherein the sample carrier further comprises a valve disposed between the sample-preparation outlet and the amplification-module inlet.

20. The system of claim 1, wherein the plurality of light sources comprises eight light sources.

\* \* \* \* \*